US006514942B1

(12) United States Patent
Ioannides et al.

(10) Patent No.: US 6,514,942 B1
(45) Date of Patent: *Feb. 4, 2003

(54) METHODS AND COMPOSITIONS FOR STIMULATING T-LYMPHOCYTES

(75) Inventors: Constantin G. Ioannides, Houston, TX (US); Bryan A. Fisk, Houston, TX (US); Maria G. Ioannides, Athens (GR)

(73) Assignee: The Board of Regents, The University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/403,459

(22) Filed: Mar. 14, 1995

(51) Int. Cl.$^7$ ................................ A61K 38/00

(52) U.S. Cl. ........................ 514/15; 530/328

(58) Field of Search ............... 530/328, 329, 530/327, 326; 514/13, 14, 15, 16

(56) References Cited

U.S. PATENT DOCUMENTS 5,534,254 A * 7/1996 Huston et al. ........... 424/135.1
5,846,538 A * 12/1998 Cheever et al. .......... 424/185.1

FOREIGN PATENT DOCUMENTS

| WO | WO9014357 | * 11/1990 |
| WO | WO9316185 | * 8/1993 |
| WO | WO9420127 | * 9/1994 |
| WO | WO9522317 | * 8/1995 |

OTHER PUBLICATIONS

Ngo et al. The Protein Folding Problem and Tertiary Structure Prediction, Merz et al. Birkhauser, Boston, MA pp 433 and 492–495, 1994.*

Aebersold et al., "Lysis of Autologous Melanoma Cells by Tumor–Infiltrating Lymphocytes: Association With Clinical Response," *Journal of the National Cancer Institute*, 83(13):932–937, Jul. 1991.

Anderson et al., "Intracellular Transport of Class I MHC Molecules in Antigen Processing Mutant Cell Lines," *The Journal of Immunology*, 151:3407–3419, Oct. 1993.

Bednarek et al., "The Minimum Peptide Epitope from the Influenza Virus Matrix Protein," *The Journal of Immunology*, 147:4047–4053, Dec. 1991.

Bednarek et al., "Soluble HLA–A2.1 restricted peptides that are recognized by influenza virus specific cytotoxic T lymphocytes," *Journal of Immunological Methods*, 139:41–47, 1991.

Bowness et al., "Conservation of T cell receptor usage by HLA B27–restricted influenza–specific cytotoxic T lymphocytes suggests a general pattern for antigen–specific major histocompatibility complex class I–restricted responses," *Eur. J. Immunol.*, 23:1417–1421, 1993.

Brichard et al., "The Tyrosinase Gene Codes for an Antigen Recognized by Autologous Cytolytic T Lymphocytes on HLA–A2 Melanomas," *J. Exp. Med.*, 178:489–496, Aug. 1993.

Carbone et al., "Induction of Cytotoxic T Lymphocytes by Primary In Vitro Stimulation with Peptides," *J. Exp. Med.*, 167:1767–1779, Jun. 1988.

DiBrino et al., "Endogenous Peptides with Distinct Amino Acid Anchor Residue Motifs Bind to HLA–A1 and HLA–B8," *Journal of Immunology*, 152:620–631, 1994.

Fisk et al., "Oligopeptide Induction of a Cytotoxic T Lymphocyte Response to HER–2/Neu Proto–oncogene in Vitro," *Cellular Immunology*, 157:415–427, 1994.

Fisk et al., "Sequence motifs on human HER–2 proto–oncogene important for peptide binding to HLA–A2," *International Journal of Oncology*, 5:51–63, 1994.

Houbiers et al., "In vitro induction of human cytotoxic T lymphocyte responses against peptides of mutant and wild–type p53," *Eur. J. Immunol.*, 23:2072–2077, 1993.

Hu et al., "An Evaluation of the Potential to Use Tumor–associated Antigens as Targets for Antitumor T Cell Therapy Using Transgenic Mice Expressing a Retroviral Tumor Antigen in Normal Lymphoid Tissues," *J. Exp. Med.*, 177:1681–1690, Jun. 1993.

Ioannides et al., "Cytotoxic T Cell Clones Isolated from Ovarian Tumor–Infiltrating Lymphocytes Recognize Multiple Antigenic Epitopes on Autologous Tumor Cells," *The Journal of Immunology*, 146(5):1700–1707, Mar. 1991.

Ioannides et al., "Cytotoxic T Cells Isolated from Ovarian Malignant Ascites Recognize a Peptide Derived from the HER–2/neu Proto–oncogene," *Cellular Immunology*, 151:225–234, 1993.

Ioannides et al., "T–Cell Recognition of Oncogene Products: A New Strategy for Immunotherapy," *Molecular Carcinogenesis*, 6:77–82, 1992.

Ioannides et al., "Tumor Cytolysis by Lymphocytes Infiltrating Ovarian Malignant Ascites," *Cancer Research*, 51:4257–4265, Aug. 1991.

(List continued on next page.)

*Primary Examiner*—Patrick J. Nolan
(74) *Attorney, Agent, or Firm*—Fulbright & Jaworski L.L.P.

(57) ABSTRACT

Disclosed are methods, compositions, antibodies, and therapeutic kits for use in stimulating cytotoxic T-lymphocytes and generating immune responses against epitopes of protooncogenes. Novel peptides are described which have been shown to stimulate cytotoxic T-lymphocytes, and act as antigens in generation of oncogenic epitope-recognizing antibodies. Methods are disclosed for use in treating various proliferative disorders, and diagnosing HER-2/neu-containing cells; also disclosed are therapeutic kits useful in the treatment of cancer and production of potential anti-cancer vaccines.

26 Claims, 11 Drawing Sheets-

OTHER PUBLICATIONS

Ioannides et al., "Cytotoxic T–Cell Clones Isolated from Ovarian Tumour Infiltrating Lymphocytes Recognize Common Determinants on Non–Ovarian Tumour Clones," *Scand. J. Immunol.*, 37:413–424, 1993.

Jerome et al., "Tumor–Specific Cytotoxic T Cell Clones from Patients with Breast and Pancreatic Adenocarcinoma Recognize EBV–Immortalized B Cells Transfected with Polymorphic Epithelial Mucin Complementary DNA," *The Journal of Immunology*, 151(3):1654–1662, Aug. 1993.

Madden et al., "The Antigenic Identity of Peptide–MHC Complexes: A Comparison of the Conformations of Five Viral Peptides Presented by HLA–A2," *Cell*, 75:693–708, Nov. 1993.

Marincola et al., "HLA Association with Response and Toxicity in Melanoma Patients Treated with Interleukin 2–based Immunotherapy," *Cancer Research*, 52:6561–6566, Dec. 1992.

Parker et al., "Sequence Motifs Important for Peptide Binding to the Human MHC Class I Molecule, HLA–A2," *The Journal of Immunology*, 149(11):3580–3587, Dec. 1992.

Ratner and Clark, "Role of TNG–α in CD8° Cytotoxic T Lymphocyte–Mediated Lysis," *The Journal of Immunology*, 150(10):4303–4314, May 1993.

Schmidt et al., "Oligopeptide Induction of a Seconary Cytotoxic T–cell Response to Esptein–Barr Virus In Vitro," *Scand. J. Immunol.*, 33:411–420, 1991.

Slamon et al., "Studies of the HER–2/neu Proto–oncogene in Human Breast and Ovarian Cancer," *Science*, 244:707–712, May 1989.

Suhrbier et al., "Peptide Epitope Induced Apoptosis of Human Cytotoxic T Lymphocytes," *The Journal of Immunology*, 159(6): 2169–2178, Mar. 1993.

Wölfel et al., "Lysis of Human Pancreatic Adenocarcinoma Cells by Autologous HLA–Class I–Restricted Cytolytic T–Lymphocyte (CTL) Clones," *Int. J. Cancer*, 54:636–644, 1993.

Zweerink et al., "Presentation of Endogenous Peptides to MHC Class I–Restricted Cytotoxic T Lymphocytes in Transport Deletion Mutant T2 Cells," *The Journal of Immunology*, 150(5):1763–1771, Mar. 1993.

* cited by examiner

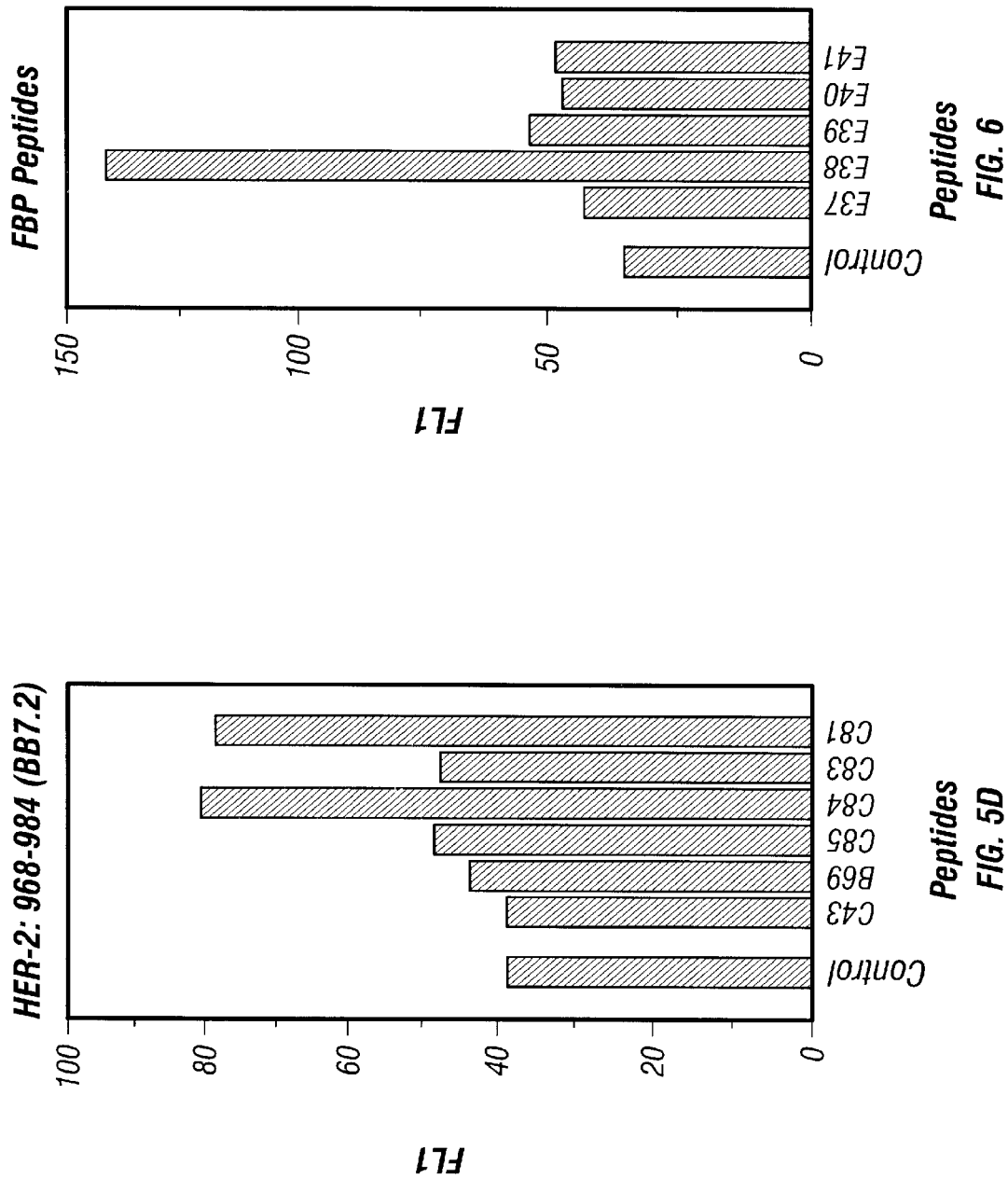

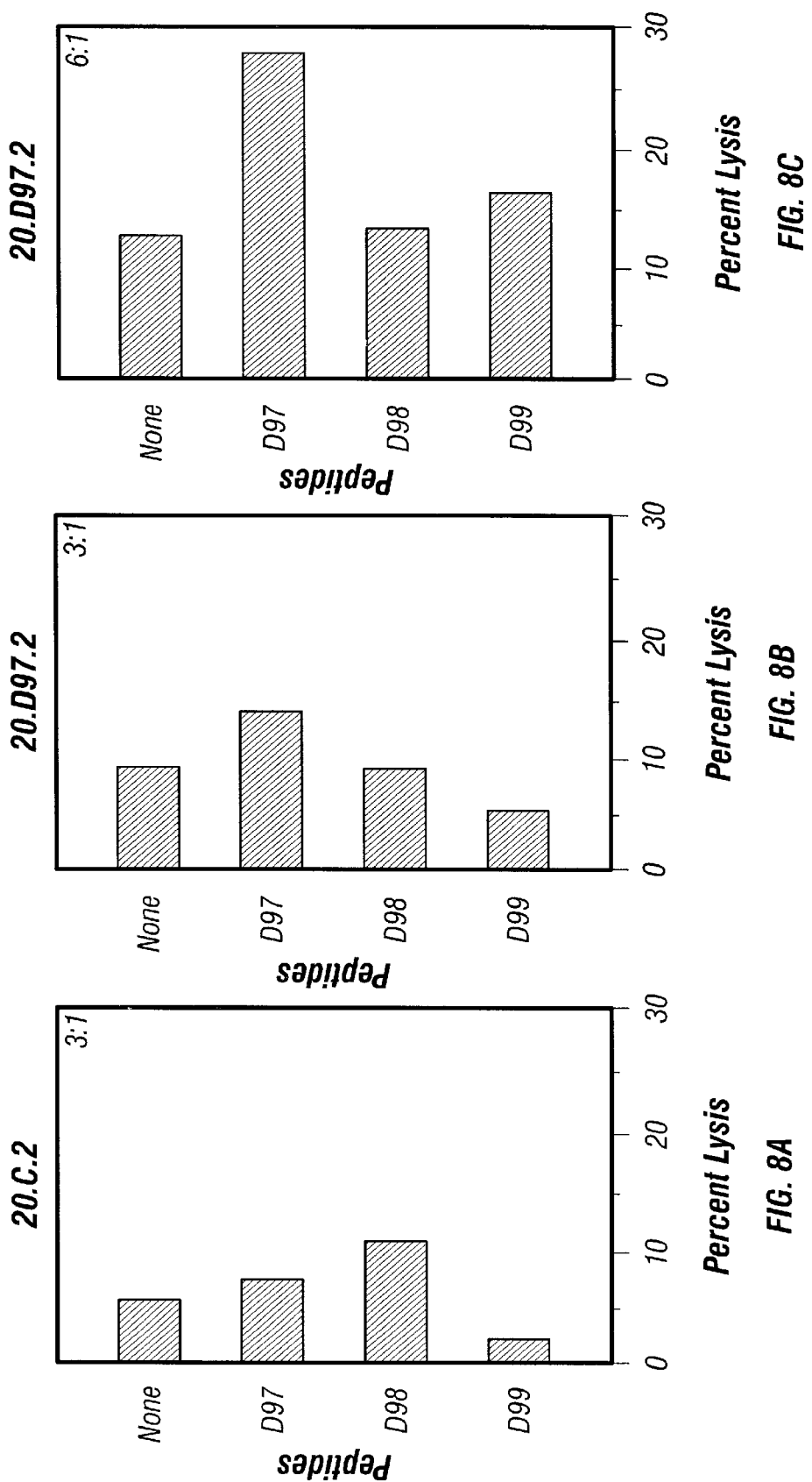

SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Glu Leu Val Lys Glu Val Ser Lys Val
1               5

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Glu Leu Val Ser Glu Val Ser Lys Val
1               5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Lys Leu Val Ser Glu Phe Ser Arg Val
1               5

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Gly Leu Val Ser Glu Phe Ser Arg Val
1               5

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear

```
        (ii) MOLECULE TYPE: peptide (xi) SEQUENCE DESCRIPTION: SEQ ID NO:5:

Glu Leu Val Ser Glu Phe Ser Lys Val
1               5

(2) INFORMATION FOR SEQ ID NO:6:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Glu Leu Val Ser Glu Phe Ser Arg Val
1               5

(2) INFORMATION FOR SEQ ID NO:7:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Glu Leu Val Ser Glu Phe Ser Arg Met
1               5

(2) INFORMATION FOR SEQ ID NO:8:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Val Leu Val Lys Ser Pro Asn His Val
1               5

(2) INFORMATION FOR SEQ ID NO:9:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Gln Leu Met Pro Tyr Gly Cys Leu Leu
1               5

(2) INFORMATION FOR SEQ ID NO:10:

(i) SEQUENCE CHARACTERISTICS:
            (A) LENGTH: 9 amino acids
            (B) TYPE: amino acid
            (C) STRANDEDNESS: single
```

(D) TOPOLOGY: linear (ii) MOLECULE TYPE: peptide (xi) SEQUENCE DESCRIPTION: SEQ ID NO:10:

Cys Leu Thr Ser Thr Val Gln Leu Val
1               5

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Lys Ile Phe Gly Ser Leu Ala Phe Leu
1               5

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Pro Leu Gln Pro Glu Gln Leu Gln Val
1               5

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Thr Leu Glu Glu Ile Thr Gly Tyr Leu
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Gln Leu Gln Val Phe Glu Thr Leu Glu
1               5

(2) INFORMATION FOR SEQ ID NO:15:

(i) SEQUENCE CHARACTERISTICS:
        (A) LENGTH: 10 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:15:

Gly Leu Gly Met Glu His Leu Arg Glu Val
1               5                   10

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Asp Leu Gly Met Gly Ala Ala Lys Gly Leu
1               5                   10

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

His Leu Tyr Gln Gly Cys Gln Val Val
1               5

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Arg Leu Leu Tyr Gln Gly Cys Gln Val Val
1               5                   10

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Gly Leu Tyr Gln Gly Cys Gln Val Val
1               5

(2) INFORMATION FOR SEQ ID NO:20:

(i) SEQUENCE CHARACTERISTICS:
        (A) LENGTH: 9 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:20:

Asp Ile Gln Glu Val Gln Gly Tyr Val
1               5

(2) INFORMATION FOR SEQ ID NO:21:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:21:

Gln Leu Arg Ser Leu Thr Glu Ile Leu
1               5

(2) INFORMATION FOR SEQ ID NO:22:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:22:

Asp Ile Phe His Lys Asn Asn Gln Leu
1               5

(2) INFORMATION FOR SEQ ID NO:23:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:23:

Tyr Ile Ser Ala Trp Pro Asp Ser Leu
1               5

(2) INFORMATION FOR SEQ ID NO:24:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:24:

Ser Leu Arg Glu Leu Gly Ser Gly Leu
1               5

(2) INFORMATION FOR SEQ ID NO:25:

(i) SEQUENCE CHARACTERISTICS:
```

(A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:25:

Pro Leu Thr Ser Ile Ile Ser Ala Val
1               5

(2) INFORMATION FOR SEQ ID NO:26:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:26:

Arg Leu Leu Gln Glu Thr Glu Leu Val
1               5

(2) INFORMATION FOR SEQ ID NO:27:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:27:

Lys Ile Pro Val Ala Ile Lys Val Leu
1               5

(2) INFORMATION FOR SEQ ID NO:28:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:28:

Gln Ile Ala Lys Gly Met Ser Tyr Leu
1               5

(2) INFORMATION FOR SEQ ID NO:29:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:29:

Thr Leu Ser Pro Gly Lys Asn Gly Val
1               5

(2) INFORMATION FOR SEQ ID NO:30:

```
        (i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:30:

His Leu Asp Met Leu Arg His Leu Tyr Gln
1               5                   10

(2) INFORMATION FOR SEQ ID NO:31:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:31:

Thr His Leu Asp Met Leu Arg His Leu Tyr Gln Gly Cys Gln
1               5                   10

(2) INFORMATION FOR SEQ ID NO:32:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:32:

Asn Gln Glu Val Thr Ala Trp Asp Gly Thr Gln Arg
1               5                   10

(2) INFORMATION FOR SEQ ID NO:33:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:33:

Leu Gln Val Phe Glu Thr Leu Glu Glu Ile Thr Gly Tyr Leu
1               5                   10

(2) INFORMATION FOR SEQ ID NO:34:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:34:

Leu Gln Pro Glu Gln Leu Gln Val Phe Glu Thr Leu Glu Glu Ile Thr
1               5                   10                  15

Gly Tyr Leu Tyr
            20
```

(2) INFORMATION FOR SEQ ID NO:35:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Gln Leu Gln Val Phe Glu Thr Leu Glu Glu Ile
1               5                  10
```

(2) INFORMATION FOR SEQ ID NO:36:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Leu Gln Pro Glu Gln Leu Gln Val Phe Glu Thr Leu Glu
1               5                  10
```

(2) INFORMATION FOR SEQ ID NO:37:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Glu Leu Val Ser Glu Phe Ser Arg Met Ala Arg
1               5                  10
```

(2) INFORMATION FOR SEQ ID NO:38:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Arg Phe Arg Glu Leu Val Ser Glu Phe Ser Arg Met Ala Arg
1               5                  10
```

(2) INFORMATION FOR SEQ ID NO:39:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Arg Phe Arg Glu Leu Ile Ile Glu Phe Ser Arg Met Ala Arg
```

```
1               5                   10
```

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

```
Leu Val Ser Glu Phe Ser Arg Met Ala Arg Asp Pro Gln
1               5                   10
```

(2) INFORMATION FOR SEQ ID NO:41:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

```
Arg Phe Arg Glu Leu Val Ser Glu Phe Ser
1               5                   10
```

(2) INFORMATION FOR SEQ ID NO:42:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

```
Glu Cys Arg Pro Arg Phe Arg Glu Leu
1               5
```

(2) INFORMATION FOR SEQ ID NO:43:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

```
Arg Phe Arg Glu Leu Val Ser
1               5
```

(2) INFORMATION FOR SEQ ID NO:44:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
Asp Leu Gly Met Gly Ala Ala Lys Gly Leu
1               5                   10
```

(2) INFORMATION FOR SEQ ID NO:45:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Phe Asp Gly Asp Leu Gly Met Gly Ala Ala Lys Gly Leu
1               5                   10
```

(2) INFORMATION FOR SEQ ID NO:46:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Arg Ile Ala Trp Ala Arg Thr Glu Leu
1               5
```

(2) INFORMATION FOR SEQ ID NO:47:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

```
Asn Leu Gly Pro Trp Ile Gln Gln Val
1               5
```

(2) INFORMATION FOR SEQ ID NO:48:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

```
Glu Ile Trp Thr His Ser Thr Lys Val
1               5
```

(2) INFORMATION FOR SEQ ID NO:49:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
Ser Leu Ala Leu Met Leu Leu Trp Leu
1               5
```

(2) INFORMATION FOR SEQ ID NO:50:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
Leu Leu Ser Leu Ala Leu Met Leu Leu
1               5
```

(2) INFORMATION FOR SEQ ID NO:51:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: one-of(4, 6, 9, 12, 18, 19, 20, 21, 24, 27)
        (D) OTHER INFORMATION: /mod_base= OTHER
            /note= "Y = C or T; N = A, G, C, or T; R = A or G; W =
            A or T; S = C or G"

(xi) SEQUENCE DESCRIPTION: SEQ ID NO:51:

```
GAAYTNGTNA ARGAAGTNWS NAARGTN                                              27
```

(2) INFORMATION FOR SEQ ID NO:52:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: one-of(4, 6, 9, 10, 11, 12, 18, 19, 20, 21, 24,
            27)
        (D) OTHER INFORMATION: /mod_base= OTHER
            /note= "Y = C or T; N = A, G, C, or T; W = A or T; S =
            C or G; R = A or G"

(xi) SEQUENCE DESCRIPTION: SEQ ID NO:52:

```
GAAYTNGTNW SNGAAGTNWS NAARGTN                                              27
```

(2) INFORMATION FOR SEQ ID NO:53:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: one-of(3, 4, 6, 9, 10, 11, 12, 18, 19, 20, 21, 22, 24, 27)
            (D) OTHER INFORMATION: /mod_base= OTHER
                /note= "R = A or G; Y = C or T; N = A, G, C, or T; W =
                A or T; S = C or G; M = A or C"

(xi) SEQUENCE DESCRIPTION: SEQ ID NO:53:

AARYTNGTNW SNGAATTYWS NMGNGTN                                                27

(2) INFORMATION FOR SEQ ID NO:54:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: one-of(3, 4, 6, 9, 10, 11, 12, 18, 19, 20, 21,
                22, 24, 27)
        (D) OTHER INFORMATION: /mod_base= OTHER
                /note= "N = A, G, C, or T; Y = C or T; W = A or T; S =
                C or G; M = A or C"

(xi) SEQUENCE DESCRIPTION: SEQ ID NO:54:

GGNYTNGTNW SNGAATTYWS NMGNGTN                                                27

(2) INFORMATION FOR SEQ ID NO:55:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: one-of(4, 6, 9, 10, 11, 12, 18, 19, 20, 21, 24,
                27)
        (D) OTHER INFORMATION: /mod_base= OTHER
                /note= "Y = C or T; N = A, G, C, or T; W = A or T; S =
                C or G; R = A or G"

(xi) SEQUENCE DESCRIPTION: SEQ ID NO:55:

GAAYTNGTNW SNGAATTYWS NAARGTN                                                27

(2) INFORMATION FOR SEQ ID NO:56:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: one-of(4, 6, 9, 10, 11, 12, 18, 19, 20, 21, 22,
                24, 27)
        (D) OTHER INFORMATION: /mod_base= OTHER
                /note= "Y = C or T; N = A, G, C, or T; W = A or T; S =
                C or G; M = A or C"

(xi) SEQUENCE DESCRIPTION: SEQ ID NO:56:

GAAYTNGTNW SNGAATTYWS NMGNGTN                                                27

(2) INFORMATION FOR SEQ ID NO:57:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: one-of(4, 6, 9, 10, 11, 12, 18, 19, 20, 21, 22, 24)
        (D) OTHER INFORMATION: /mod_base= OTHER
            /note= "Y = C or T; N = A, G, C, or T; W = A or T; S = C or G; M = A or C"

(xi) SEQUENCE DESCRIPTION: SEQ ID NO:57:

GAAYTNGTNW SNGAATTYWS NMGNATG                                         27

(2) INFORMATION FOR SEQ ID NO:58:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: one-of(3, 4, 6, 9, 12, 13, 14, 15, 18, 21, 24, 27)
        (D) OTHER INFORMATION: /mod_base= OTHER
            /note= "N = A, G, C, or T; Y = C or T; R = A or G; W = A or T; S = C or G"

(xi) SEQUENCE DESCRIPTION: SEQ ID NO:58:

GTNYTNGTNA ARWSNCCNAA YCAYGTN                                         27

(2) INFORMATION FOR SEQ ID NO:59:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: one-of(3, 4, 6, 12, 15, 18, 21, 22, 24, 25, 27)
        (D) OTHER INFORMATION: /mod_base= OTHER
            /note= "R = A or G; Y = C or T; N = A, G, C, or T; R = A or G;"

(xi) SEQUENCE DESCRIPTION: SEQ ID NO:59:

CARYTNATGC CNTAYGARTG YYTNYTN                                         27

(2) INFORMATION FOR SEQ ID NO:60:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:

(A) NAME/KEY: modified_base
(B) LOCATION: one-of(3, 4, 6, 9, 10, 11, 12, 15, 18, 21, 22, 24, 27)
(D) OTHER INFORMATION: /mod_base= OTHER
    /note= "Y = C or T; N = A, G, C, or T; W = A or T; S = C or G; R = A or G"

(xi) SEQUENCE DESCRIPTION: SEQ ID NO:60:

TGYYTNACNW SNACNGTNCA RYTNGTN                                       27

(2) INFORMATION FOR SEQ ID NO:61:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: modified_base
       (B) LOCATION: one-of(3, 6, 9, 12, 13, 14, 15, 16, 18, 21, 24, 25, 27)
       (D) OTHER INFORMATION: /mod_base= OTHER
           /note= "R = A or G; H = A, C, or T; Y = C or T; N = A, G, C, or T; W = A or T; S = C or G"

(xi) SEQUENCE DESCRIPTION: SEQ ID NO:61:

AARATHTTYG GNWSNYTNGC NTTYYTN                                       27

(2) INFORMATION FOR SEQ ID NO:62:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: modified_base
       (B) LOCATION: one-of(3, 4, 6, 9, 12, 15, 18, 19, 21, 24, 27)
       (D) OTHER INFORMATION: /mod_base= OTHER
           /note= "N = A, G, C, or T; Y = C or T; R = A or G"

(xi) SEQUENCE DESCRIPTION: SEQ ID NO:62:

CCNYTNCARC CNGARCARYT NCARGTN                                       27

(2) INFORMATION FOR SEQ ID NO:63:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: modified_base
       (B) LOCATION: one-of(3, 4, 6, 9, 12, 15, 18, 21, 24, 25, 27)
       (D) OTHER INFORMATION: /mod_base= OTHER
           /note= "N = A, G, C, or T; Y = C or T; R = A or G; H = A, C, or T;"

(xi) SEQUENCE DESCRIPTION: SEQ ID NO:63:

ACNYTNGARG ARATHACNGG NTAYYTN                                       27

(2) INFORMATION FOR SEQ ID NO:64:

```
        (i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: modified_base
             (B) LOCATION: one-of(3, 4, 6, 9, 12, 15, 18, 21, 22, 24)
             (D) OTHER INFORMATION: /mod_base= OTHER
                 /note= "R = A or G; Y = C or T; N = A, G, C, or T"

(xi) SEQUENCE DESCRIPTION: SEQ ID NO:64:

CARYTNCARG TNTTYGARAC NYTN                                          24

(2) INFORMATION FOR SEQ ID NO:65:

(i) SEQUENCE CHARACTERISTICS:
             (A) LENGTH: 14 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:65:

Arg Phe Arg Glu Leu Val Ser Glu Phe Ser Arg Met Ala Arg
1               5                   10

(2) INFORMATION FOR SEQ ID NO:66:

(i) SEQUENCE CHARACTERISTICS:
             (A) LENGTH: 14 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:66:

Arg Phe Arg Glu Leu Ile Ile Glu Phe Ser Arg Met Ala Arg
1               5                   10

(2) INFORMATION FOR SEQ ID NO:67:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:67:

Ser Leu Ala Asp Pro Ala His Gly Val
1               5

(2) INFORMATION FOR SEQ ID NO:68:

(i) SEQUENCE CHARACTERISTICS:
             (A) LENGTH: 10 amino acids
             (B) TYPE: amino acid
             (C) STRANDEDNESS: single
             (D) TOPOLOGY: linear
```

```
    (ii) MOLECULE TYPE: peptide (xi) SEQUENCE DESCRIPTION: SEQ ID NO:68:

Gly Leu Thr Ser Ala Pro Asp Thr Arg Val
1               5                   10
```

METHODS AND COMPOSITIONS FOR STIMULATING T-LYMPHOCYTES

The United States government owns rights to the present invention pursuant to Grants CA 57293 and CA 16672 from the National Cancer Institute.

BACKGROUND OF THE INVENTION

A. Field of the Invention

The present invention relates generally to the field of molecular biology, and particularly to the area of natural and synthetic peptides. More particularly, the invention discloses HER-2/neu peptide, DNA segment, antibody compositions. Various methods for making and using these compositions are disclosed, such as, for example, the use of peptides and antibodies in various pharmacological and immunological applications, including the stimulation of cytotoxic T-lymphocytes and cancer therapies.

B. Description of the Related Art

1. HER-2/neu Proto-Oncogene

The HER-2/neu proto-oncogene (HER-2) encodes a transmembrane protein whose expression is enhanced in a number of breast and ovarian tumors and correlates with tumor aggressiveness. Because of its expression on normal epithelial cells, HER-2 can be defined as a tumor-associated antigen (Ag) and may be of interest as a target of a therapeutic anti-tumor T-cell response. A $CD3^+CD8^+CD4^-$ line isolated from cell cultures has been shown to lyse $HLA-A2^+$, $HER-s^+$ ovarian tumors but not natural killer (NK) target K562 cells, and showed significantly higher lysis of $HER-2^{high}$ than of $HER-2^{low}$ ovarian tumors. Some inhibition of lysis was inhibited by HER-2 peptide-pulsed $HLA-A2^+$ targets, suggesting that some epitopes may be present on tumor cells associated with HLA-A2.

2. Tumor-Reactive T-Cells

Tumor reactive T-cells have been reported to mediate therapeutic responses against human cancers (Rosenberg et al., 1988). In certain instances, in human immunotherapy trials with tumor infiltrating lymphocytes (TIL) or tumor vaccines, these responses correlated either with in vitro cytotoxicity levels against autologous tumors (Aebersold et al., 1991) or with expression of certain HLA-A,B,C gene products (Marincola et al., 1992). Recent studies (Ioannides et al., 1992) have proposed that in addition to virally encoded and mutated oncogenes, overexpressed self-proteins may elicit some degree of tumor-reactive cytotoxic T-lymphocytes (CTLs) in patients with various malignancies (Ioannides et al., 1992; Ioannides et al., 1993; Brichard et al., 1993; Jerome et al., 1991). Autologous tumor reactive CTLs can be generated from lymphocytes infiltrating ovarian malignant ascites (Ioannides et al., 1991), and overexpressed proteins such as HER-2 may be targets for CTL recognition (Ioannides et al., 1992).

Information on epitopes of self-proteins recognized in the context of MHC Class I molecules remain limited, despite a few attempts to identify epitopes capable of in vitro priming and Ag-specific expansion of human CTLs. For example, peptide epitopes have been proposed which are likely candidates for binding on particular MHC Class I Ag (Falk et al., 1991), and some studies have attempted to define peptide epitopes which bind MHC Class I antigens.

Short synthetic peptides have been used either as target antigens for epitope mapping or for induction of in vitro primary and secondary CTL responses to viral and parasitic Ags (Bednarek et al., 1991; Gammon et al., 1992; Schmidt et al., 1992; Kos and Müllbacher, 1992; Hill et al., 1992). Unfortunately, these studies failed to show the ability of proto-oncogene peptide analogs to stimulate in vitro human CTLs to lyse tumors endogenously expressing these antigens.

3. Synthetic Peptides and T-Cell Epitope Mapping

Synthetic peptides have been shown to be a useful tool for T-cell epitope mapping. However in vivo and in vitro priming of specific CTLs has encountered difficulties (Alexander et al., 1991; Schild et al., 1991; Carbone et al., 1988). It is generally considered that in vitro CTL priming cannot necessarily be achieved with peptide alone, and in fact, a high antigen density is thought to be required for peptide priming (Alexander et al., 1991). Even in the limited instances when specific priming was achieved, APC or stimulators were also required at high densities (Alexander et al., 1991).

It is not clear when CTL induction by HER-2 peptides in vitro was observed whether this reflects secondary activation of CTL specific for, or cross-reacting with, the Ag of interest. Whether or not this cross-reactivity can constitute the foundation for development of an in vitro CTL response to tumor remains to be determined.

Therefore, what is lacking in the prior art are universal epitopes which are both immunodominant and CTL-stimulating. Moreover, methods for the use of such CTL-stimulating peptides would be most desirable in the treatment of human cancers, particularly of breast and ovarian etiology, and the development of cancer vaccines. Identifying universal oncoprotein epitopes would permit not only an increased understanding of tumor immunity and autoimmunity in humans, but would also open the door to the design of novel therapeutic strategies for proliferative cell disorders such as human cancers, and particularly breast and ovarian cancers.

SUMMARY OF THE INVENTION

The present invention seeks to overcome these and other inherent deficiencies in the prior art by providing the identification of native and synthetic proteins or peptides derived from the HER-2/neu proto-oncogene gene product, and methods for their use in stimulating cytotoxic T-lymphocytes. These selected "universal" immunodominant epitopic peptides, and their synthetically-optimized derivatives are envisioned to be useful in the development of tumor vaccines, and anti-cancer therapeutics. Pharmaceutical reagents resulting from these novel peptides and the DNA segments which encode them will also likely prove useful as test reagents for the detection of HER-2/neu-related polypeptides, facilitate the production of anti-peptide antibodies specific to a range of HER-2/neu-related polypeptides, and result in the stimulation and production of cytotoxic T-lymphocytes specific for a variety of proliferative disorders including human cancer.

Synthetic peptide analogs can be used to define CTL epitopes recognized by tumor reactive T-cells and to stimulate in vitro peptide-specific CTLs. Such CTLs can be further evaluated for recognition of targets endogenously expressing the particular antigen (Ag) and for Ag-specific adoptive therapy.

Disclosed herein are compositions and methods for their making and use in development of anti-cancer vaccines. The generation in vitro of HLA-A2-restricted CTLs using HER-2 synthetic peptide analogs as immunogens, and peripheral blood mononuclear cells (PBMC) from healthy volunteers as responder cells is also described. Lysis with isolated CD8$^+$ T-cells from these CTL cultures was observed using both HER-2 peptide-pulsed HLA-A2 from these CTL cultures was observed using both HER-2 peptide-pulsed HLA-A2 transfectants and HLA-A2$^+$ ovarian tumors expressing high levels of HER-2 as targets.

Another aspect of the invention is the development and maintenance in long-term culture a CD3$^+$CD8$^+$CD4$^-$ line by restimulation with HER-2 peptide-pulsed autologous PBMC. This line lysed HLA-A2$^+$, HER-2$^{high}$ ovarian tumors, but not HLA-A2$^+$, HER-2$^{low}$ ovarian tumors. Tumor lysis was inhibited by HER-2 peptide-pulsed HLA-A2$^+$ transfectants, demonstrating that epitopes either similar or cross-reactive with the ones recognized by CTLs on the peptide used as immunogen in vitro are present on the tumor cells. These CTL showed lower lysis of targets pulsed with unrelated peptides (analogs of Muc-1 core peptide where HLA-A2 anchors were introduced).

A novel approach to developing tumor reactive CTLs is disclosed which focuses on a target Ag expressed on the tumor of interest and identifying CTLs induced in vivo or developed in vitro that recognize this target Ag. In tumor cells the level of expression of a particular protein may be $10^2$–$10^3$ fold higher than in normal tissue.

The inventors expect that a number of target T-cell Ags on human tumors may be derived from proteins that are expressed at low levels in normal cells, and at significantly higher concentration in tumor cells, such as overexpressed proto-oncogene products (Ioannides et al., 1992). The rationale for this hypothesis is: first, peptides from self-proteins which fulfill the criteria of MHC allele-specific motifs should be capable of binding to the Ag binding pockets in the MHC class I heavy chain; and second, positive and negative selection of T-cell repertoire may result in elimination or tolerization of high-affinity self-reactive CTLs (Parmianai, 1993), although such peptide-MHC complexes should have lower affinity for the TCR than a de novo expressed epitope from a self-protein (as a consequence either of mutations creating HLA-anchors or modifying the core recognized by the TCR), their presence in high concentration may engage a large number of TCR.

The HER-2/neu proto-oncogene was identified because it is overexpressed (in certain instances by several hundred fold) in a number of breast and ovarian tumors (Slamon et al., 1989). Moreover, it was found that several CTL-TAL lines isolated from ovarian malignant ascites could lyse autologous ovarian tumors.

Surprisingly, the inventors also discovered that this lysis could also be effectively inhibited by natural and synthetic peptide analogs of HER-2. These results suggested that these novel peptides acted as epitopes that were either derived from an endogenously-processed HER-2 peptide, mimicked, or cross-reacted with a peptide of related sequence derived from another protein.

Novel synthetic peptide compositions have also been developed which correspond to the HER-2:968–981 and 971–979 regions. The compositions disclosed herein, were found to stimulate in vitro PBMCs from healthy HLA-A2$^+$ human volunteers (Fisk et al., 1994), and CTLs (induced by peptide stimulation) consequently lysed tumors overexpressing HER-2 (Fisk et al., 1994). These studies demonstrated that these CTLs can effectively recognize the epitope peptides of the present invention, and that these HER-2-derived peptides can stimulate in vitro PBMCs to induce peptide reactive CTLs.

This possibility may be particularly relevant for induction of Ag and tumor-specific CTLs because peripheral T-cells that can recognize such peptides from non-mutated self proteins are those that have either escaped elimination or may have become tolerant to one or more of these antigenic epitopes due to low affinity TCR-MHC interactions (Ioannides et al., 1992; Parmiani, 1993).

Other aspects of this invention include the identification of candidate HER-2-derived T-cell epitopes based on the presence of anchors for HLA-A2, the analysis of these peptides to affect the conformation of HLA-A2 as an indication of peptide binding, and finally, the demonstration that these peptides can stimulate in vitro peptide reactive CTLs from human HLA-A2$^+$ PBMC.

Methods are described herein for stimulation of CTLs (and consequently, production of an immune response) employing the novel compositions disclosed herein. In vitro induction of cellular responses to the peptides of the present invention by PBMC from healthy HLA-A2$^+$ volunteers demonstrated their ability to stimulate and/or restimulate pre-existing T-cell responses to HER-2. The peptides induced proliferative responses in one of four donors tested and CTL responses (one of three peptides tested in two of three donors), and may be used to induce tumor-reactive T-cells in vitro and in vivo through either peptide-, lipopeptide-, or cell-mediated methods. These peptides therefore find utility in both generating an immune response, and serving as antigens in the preparation of peptide-specific antibodies.

The peptides of this invention also may be used in embodiments involving treatment, diagnosis, and identification of proliferative cell disorders such as cancer, and particularly cancers such as, inter alia, breast and ovarian tumors. Methods of identification of HER-2/neu-containing cells, and also neu-related proto-oncogene and oncogene products are also disclosed.

Cancer treatment methods, including vaccine development are another aspect of the present invention. Additionally, a variety of in vitro and in vivo assay protocols are facilitated as a result of the novel compositions disclosed herein. In addition to stimulating CTLs, and generating an immune response in an animal, and particularly in a human, the peptides may also be used as immunogens to generate anti-peptide antibodies, which themselves have many uses, not least of which is the detection of oncogene-containing cells (e.g., detection of HER-2/neu, related oncogenic polypeptides, or peptide fragments thereof, in diagnostic tests and kits based upon immunological binding assays).

Also, since the peptides of the invention bind to T-cells, they may be employed in assays to identify T-cells, and particularly CTLs, for example, to assess the immunological capacity of a given individual or animal, or even to purify CTLs themselves. Such methods could utilize radioactively- or enzymatically-labeled peptides or anti-peptide antibodies, such as those described herein.

Therefore, one contemplated use for the described peptides concerns their use in methods for detecting the presence of T-cells within a sample. These methods include contacting a sample suspected of containing T-cells with a peptide or composition in accordance with the present invention under conditions effective to allow the peptide(s) to form a complex with T-cells of the sample. One then detects the presence of the complex by detecting the presence of the peptide(s) within the complex, e.g., by either originally using radiolabeled peptides or by subsequently employing anti-peptide antibodies and standard secondary antibody detection techniques.

Preferred peptides of the present invention will likely be from about 6 to about 20 amino acids, in length, with peptides of from 7 to about 15 amino acids in length being even more preferred. Most preferred are peptides having lengths of from about 8 to about 10 amino acids in length, with nonameric and decameric peptides being most preferred. These peptides may include one or more D-amino acids, or may even be entirely composed of D-amino acids, and may, of course, contain additional elements, as desired for stability or even for targeting purposes.

The peptides, or multimers thereof, may be dispersed in any one of the many pharmacologically-acceptable vehicles known in the art and particularly exemplified herein. As such, the peptides may be encapsulated within liposomes or incorporated in a biocompatible coating designed for slow-release. The preparation and use of appropriate therapeutic formulations will be known to those of skill in the art in light of the present disclosure. The peptides may also be used as part of a prophylactic regimen designed to prevent, or protect against, possible cancer progression and/or metastasis and may thus be formulated as a vaccine, particularly as a method of stimulating anti-tumor CTLs.

The present invention also provides methods for identifying HER-2/neu and related proto-oncogene products, which methods comprise contacting the cells suspected of containing such polypeptides with an immunologically effective amount of a composition comprising one or more specific anti-peptide antibodies disclosed herein. Peptides that include the amino acid sequence of any of SEQ ID NO:1 through SEQ ID NO:29 and their derivatives will be preferred for use in generating such anti-CTL-stimulating peptide antibodies.

The invention thus also provides compositions, including peptides, peptide multimers, and pharmaceutical compositions derived therefrom, that contain one or more peptides of from 8 to about 20 amino acids in length that include within their sequence the peptide sequence identified by the formula: $AA_1$-$AA_2$-$AA_3$-$AA_4$-$AA_5$-$AA_6$-$AA_7$-$AA_8$; where $AA_1$ is Leu, Met, Ile, or Val; $AA_2$ is any amino acid; $AA_3$ is any amino acid; $AA_4$ is Ser, Glu, Thr, or Tyr; $AA_5$ is any amino acid; $AA_6$ is any amino acid; $AA_7$ is any amino acid; and $AA_7$ is Val, Leu, Met, Ile, or Cys. These peptides are submitted to be capable of stimulating CTLs and producing an immune response in vitro and in vivo.

Another aspect of the present invention concerns the use of the amino acid sequences disclosed herein in the determination of molecular weights of low-molecular-weight polypeptides. These peptides represent a significant improvement over commercially-available protein standards in this area owing to their small size, and the presence of known nonapeptide motifs. Commercially-available standards typically have a range of 3,000 to 200,000 Da, and as such, are not useful in the characterization of proteins having molecular weights of about 300 to about 3,000 Da using either conventional or gradient SDS-PAGE.

In a similar fashion, the peptides, and more particularly peptide oligomers, of the present invention are readily employed as standards in the identification of small molecular-weight polypeptides using chromatographic separation. In preferred embodiments, paper chromatography is utilized and proteins are subsequently visualized after reaction with ninhydrin. More preferred is the use of thin-layer chromatography in either one or two dimensions.

The use of the peptides and peptide motifs of the present invention is also contemplated for the calibration and standardization of chromatographic columns used in the separation of low-molecular-weight polypeptides. These peptides, and multimers thereof, find important use in the calibration of low-molecular-weight-range columns. Such molecular sieve (or gel filtration) chromatography columns may include a filtration medium having the capacity to fractionate any protein of interest and the peptides of the present invention. Preferred chromatographic media would include any gel filtration medium having a molecular fractionation range suitable for the particular protein of interest. Preferred media would include the G-50 or G-25 Sephadex® resins which have an approximate fractionation range of 1,500–30,000 and 100–5,000 Da, respectively. A more preferred medium would be either the G-10 or G-15 Sephadex® resins which have an approximate fractionation range of 0–700 and 0–1500 Da, respectively.

Peptides of the present invention comprising aromatic amino acids and multimers thereof may also be used as protein concentration standards in reactions employing either the Folin reagent (Lowry et al., 1951), the biuret reaction (Coakley and James, 1978) or the bicinconinic acid assay (Pierce Chemical Corp., Rockford, Ill.). Peptides and multimers thereof lacking aromatic amino acids may also be used as protein concentration standards in the latter two reactions.

BRIEF DESCRIPTION OF THE DRAWINGS

FIG. 2A. Ag specificity of the 41.CD8$^+$ CTL line. C1R:A2 cells were pre-pulsed with either HER-2 peptides or control MUC-1 peptides before being incubated with effectors. The effector to target ratio was 10:1. C1R:A1 and C1R:A3 targets were pre-pulsed with the same peptides in the same conditions as C1R:A2 cells. Results for C1R:A1 and C1R:A3 show the difference between specific lysis of targets preincubated with peptides and control C1R:A1 and C1R:A3 targets. Specific lysis of control C1R:A1 and C1R:A3 cells was less than 10% at the same E:T ratio. Shown in FIG. 2A are results after 4 hrs' incubation.

FIG. 2B. Ag specificity of the 41.CD8+ CTL line. C1R:A2 cells were pre-pulsed with either HER-2 peptides or control MUC-1 peptides before being incubated with effectors. The effector to target ratio was 10:1. C1R:A1 and C1R:A3 targets were pre-pulsed with the same peptides in the same conditions as C1R:A2 cells. Results for C1R:A1 and C1R:A3 show the difference between specific lysis of targets preincubated with peptides and control C1R:A1 and C1R:A3 targets. Specific lysis of control C1R:A1 and C1R:A3 cells was less than 10% at the same E:T ratio. Shown in FIG. 2B are results after 20 hrs incubation.

FIG. 5D. Effects of HER-2 peptides on reactivity of BB7.2 mAb with T2 cells. Studies were performed as described in the legend to FIG. 5A.

FIG. 6. Effects of Folate Binding Protein (FBP) peptides on reactivity of MA2.1 mAb with T2 cells. Experimental conditions as described in the legend to FIG. 5A. Control column indicates that T2 cells were cultured in the absence of peptide.

FIG. 8A. CTL induction by HER-2 D97 peptide. PBMC from donor 20 were induced in vitro with mock stimulated medium only (20.C.2). After two cycles of stimulation CTL activity was determined in a 4 h $^{51}$Cr release assay using as targets C1R:A2 cells pulse-labelled with the indicated peptides (D97, D9, D99) or in the absence of peptide (none).

FIG. 8B. CTL induction by HER-2 D97 peptide. PBMC from donor 20 were induced in vitro with D97 (20.D97.2), at a ratio of 3:1. Studies were performed as described in the legend to FIG. 8A.

FIG. 8C. CTL induction by HER-2 D97 peptide. PBMC from donor 20 were induced in vitro with D97 (20.D97.2), at a ratio of 6:1. Studies were performed as described in the legend to FIG. 8A.

DETAILED DESCRIPTION OF THE PREFERRED EMBODIMENTS

1. Molecular Therapies for Cancer

Figure 1C:
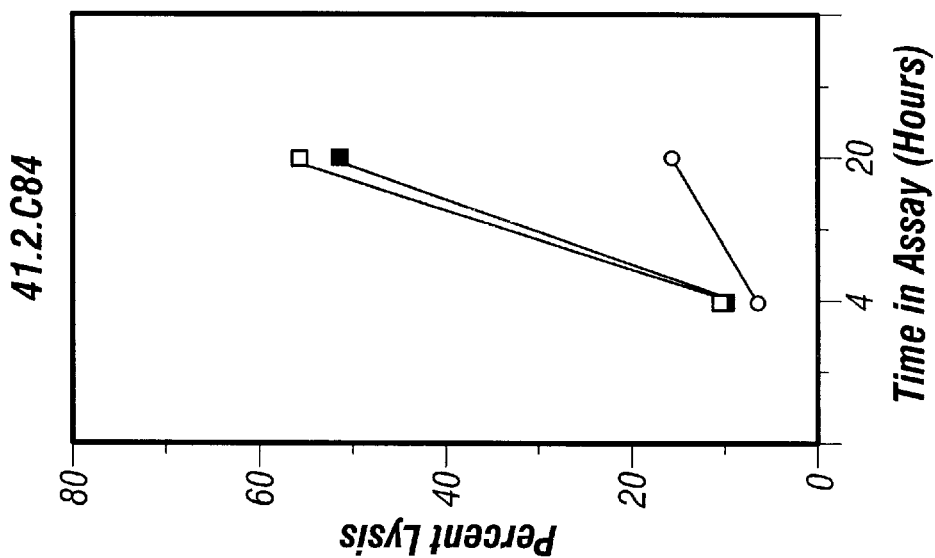
FIG. 1C. Lysis of C1R:A2 cells after sensitization with peptides C43 (HER-2:968–981) (■) and C84 (HER-2:921–979(Val) (□) or in the absence of exogenously added peptides (0) by CTL cultures induced in vitro with C43 and C84 peptides. Headings indicate: donor number (e.g., 51), number of stimulations with peptide (e.g., 2×/3×), and the peptide used for stimulation. Shown is the donor 41 PBMC stimulated two times with C84.

Development of molecular therapies for cancer have historically focused on specific recognition of Ags by cellular immune effectors. The present invention discloses novel strategies aimed at identification of peptide targets for CTLs, and generation of T-cell immunity against specific epitopes (for a review of T-cell specific immunity, see, e.g., Ioannides et al., 1992; Houbiers et al., 1993).

To achieve this, the present invention provides novel naturally- and synthetically-derived peptides which bind human leucocyte antigen-(HLA) class I heavy chains. Appropriate criteria for epitope selection in vitro have been defined. Using HER-2 protein (which has been proposed as a candidate for an anti-tumor immune response in breast and ovarian cancer) these novel peptides have been identified, isolated away from intact HER-2 protein and characterized. Additionally, synthetic peptides based on immunogenic epitopes of the HER-2 protein have also been produced.

Although the dominant anchors for peptide binding to HLA-A2 are Leu (P2) and Val (P9), a number of residues with similar charge and side chains such as Ile and Met were identified in CTL epitopes from viral proteins (Falk et al., 1991; Bednarek et al., 1991). Analysis of the HER-2 polypeptide sequence identified a large number of nonapeptides meeting these criteria (Table 1). With few exceptions, all HLA-A2 binding peptides identified in the present invention contain Rothbard's epitope-motifs. In a few instances, however, the peptide sequence contained between HLA-A2 anchors matched or overlapped with amphiphilic areas.

Using more stringent selection criteria, in which only Leu/Ile were accepted at amino acid position 2 of the peptide ($AA_2$) and at least one additional anchor was required, seventeen novel sequences were found, 10 of which contained Leu and Val at $AA_2$ and $AA_9$ respectively. Most of these sequences (shown in Table 2) were adjacent to potential amphiphilic sites.

Because it is well-known that not all HLA-A2 anchor-containing peptides are antigenic, and that it was generally considered not possible to generate antigens from very short peptide sequences (such as, e.g., peptides shorter than eight amino acids) the discovery by the inventors that these nonameric peptides both recognized CTLs, stimulated them, and produced an immune response was indeed a surprising discovery.

Three criteria of epitope selection and identified the effects of peptide length and presence of anchors on reactivity of HLA-A2 with MA2.1 mAb. MA2.1 mAb recognizes an epitope made of residues 62–65 of the α1 helix which is left to the center of the binding site on HLA-A2 (Santon-Aguado et al., 1988). Therefore exogenous peptide binding to HLA-A2 may have three potential consequences:

(a) induction of a conformational epitope by binding to an 'empty' HLA-A2 molecule, or displacing a pre-existing endogenous peptide in which case MA2.1 mAb reactivity with HLA-A2 will increase;

(b) prevention of reactivity of MA2.1 with its epitope either by obscuring residues with which the mAb may interact or interfering with mAb epitope interaction, in which case MA2.1 mAb reactivity with its epitope will decrease (Hogquist et al., 1993); and, (c) no effect in reactivity of MA2.1 mAb with HLA-A2 in which case the exogenous added peptide may displace the existing endogenous peptide, but the conformation of the 'face' made of α1-peptide-α2 will not change. In this case conformational changes on the MHC heavy chain may be detected in a different position using another mAb such as BB7.2 which interacts with an epitope containing W(108) (Salter et al., 1987).

Another surprising aspect of the invention was the fact that when long peptides (such as, e.g., peptides longer than 20 amino acids) were used which contained within their sequences peptide sequences which are disclosed herein, these >20 amino acid peptides failed to induce changes in FL1 while the novel compositions disclosed herein, effectively induced FL1 changes. This suggests that peptides >20 amino acids (1) either fail to bind to MHC heavy chain because of low affinity, (2) fail to be processed to shorter peptides because of either absence of extracellular proteases secreted by T2 cells or (3) lack the correct sites in the substrate for processing by extracellular proteases.

The highest increase in FL1 was induced by a D113 analog containing G (P1) replacing the bulky and hydrophilic H (P1), suggesting that residues at P1 may interfere either with mAb or peptide binding. Val (P9) appeared to be important for MA2.1 epitope induction because substitution M→V (P9) induced an increase in FL1 compared with the wild-type nonapeptide C85 (971–979).

The D97 reactive CTLs identified, as well as the previously demonstrated C85 reactive CTLs, indicate that T-cells reactive with these epitopes are not clonally deleted, while the possible anergic state of self-reactive CTLs from peripheral blood may have been overcome by using PBMC at high density as APC. The use of PBMC as APC may have selective advantages over T2 or C1R:A2 used in other studies (Fisk et al., 1994; Houbiers et al., 1993). First, a number of cells from PBMC can either present Ag, or release lymphokines, or in general provide help for CTL induction; second, they reflect closer the situation encountered during in vivo vaccination with tumor peptides than T2/C1R:A2 cells; and third, induction of peptide reactive T-cell may not only identify epitopes able to induce a response to a tumor Ag but also re-stimulate in vivo primed T-cells. These cells can either recognize, or cross-react with epitopes from HER-2 or from other proteins which mimic the corresponding HER-2 epitopes; fourth, by determining the frequency of such responses among healthy HLA-A2$^+$ donors, this may allow identification of changes in the responder frequency in breast and ovarian cancer patients with HER-2 high and HER-2 low expression on their tumors.

No direct correlation could be demonstrated between the ability of these peptides to affect the MA2.1 epitopes and either their ability to stimulate lymphocyte proliferation or to induce in vitro CTLs specific for the peptide of interest. Both D113 and D119 as well as longer peptides when used as immunogen to stimulate PBMC in vitro failed to induce a sustained Ag specific CTL response. In cytotoxicity assays, the PBMC cultures stimulated with these peptides failed to show preferential recognition of Ag used for stimulation. In Example 1 it is shown that HER-2:968–981 or HER-2:971–979 peptides can induce a CTL response in vitro. Therefore the inability of peptides HER-2:2:48–56 and HER-2:402–410 to induce in vitro Ag specific CTL may reflect: (1) clonal deletion of epitope reactive CD8$^+$ CTL; (2) anergy or suppression of specific CTL clones; or (3) inefficient Ag presentation in the sense that the peptide although increases the number of MA2.1 epitopes and apparently stabilizes HLA-A2 its conformation does not provide efficient signaling through TCR (Hogquist et al., 1993).

2. CTL Epitopes

CTL epitopes reported to date are mainly derived from foreign (viral) proteins with little or no homology with self-proteins. With respect to CTL responses to self-proteins, it is expected that T-cells expressing TCR with high affinity for self-peptide-MHC class I complexes are eliminated in the thymus during development. Self-peptides eluted from HLA-A2.1 molecules of various cell lines show residues at P3–P5 and P7–P8 which are different from the sequences of viral epitopes recognized by human CTLs. Since these residues are likely to contact and interact with TCR, they may reflect peptides for which autologous T-cells are already tolerant/anergic.

For T-cell recognizing self-epitopes to be eliminated or anergized, a precondition exists that the peptide-MHC complex is stable enough to engage a sufficient number of TCRs, or at least more stable than other HLA-A2 peptide complexes, where one peptide can be easily displaced by other peptides. Consequently this would suggest that for self-proteins with extension to HER-2, the ones that can bind TCR with high affinity during development will be less likely to be recognized later when expressed on a tumor other target, than peptides that bind HLA-A2 with low affinity, which under appropriate conditions (e.g., high protein concentration) may occupy a higher number of HLA-A2 molecules. For low-affinity peptides, modification of the anchors resulting in stabilization of peptide—HLA-A2 interaction by replacing weak with dominant anchor residues (e.g., (P9) M→V, should facilitate the reactivity of CTL with targets expressing such antigens, because TCR interacts mainly with the sequence P4–P8.

Tumor progression and metastasis are often associated with overexpression of specific cellular proteins. Epitopes of non-mutated overexpressed proteins can be targets of a specific cellular immune response against tumor mediated by T-cells. Moreover, when T-cell epitopes are present, distinction between tumor immunity/autoimmunity and unresponsiveness can be predicated on the protein concentration as a limiting factor of epitope supply. The present inventors have demonstrated that CTLs from patients with ovarian tumors which over-express HER-2 proto-oncogene can recognize both autologous tumor and novel synthetic analogs of a specific HER-2 epitopes. These epitopes were identified in HER-2 containing nonapeptides with HLA-A2 anchors. Analysis of potential amphiphilic sites identified natural peptides and novel synthetic peptides which surprisingly affected the reactivity of conformationally-dependent HLA-A2 specific monoclonal antibodies (mAbs), and indicated specific binding of these peptides similar to that seen for HER-2 epitopes.

3. Screening Kits

In another aspect, the present invention contemplates a diagnostic kit for screening samples suspected of containing HER-2/neu or neu-related polypeptides, or cells producing such polypeptides. Said kit can contain a peptide or antibody of the present invention. The kit can contain reagents for detecting an interaction between an agent and a peptide or antibody of the present invention. The provided reagent can be radio-, fluorescently- or enzymatically-labeled. The kit can contain a known radiolabeled agent capable of binding or interacting with a peptide or antibody of the present invention.

In another aspect, the present invention contemplates a diagnostic kit for detecting CTLs. The kit comprises reagents capable of detecting a peptide of the present invention and a CTL. The provided reagent may also be radio-, enzymatically-, or fluorescently-labeled. The kit can contain a radiolabeled peptide capable of binding to or interacting with a CTL, or may contain a radiolabeled antibody capable of binding to or interacting with a peptide of the present invention which in turn interacts with a CTL. The kit can contain a polynucleotide probe from about 15 to 60 nucleotides that encodes a peptide of the present invention or any of their complements. The kit can contain an antibody immunoreactive with a peptide of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

4. Immunodetection Kits

In still further embodiments, the present invention concerns immunodetection methods and associated kits. It is proposed that the CTL-stimulating peptides of the present invention may be employed to detect antibodies having reactivity therewith, or, alternatively, antibodies prepared in accordance with the present invention, may be employed to detect CTLs or neu-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For diagnostic purposes, it is proposed that virtually any sample suspected of comprising either the HER-2/neu peptide or neu-related peptides or antibody sought to be detected, as the case may be, may be employed. Exemplary samples include clinical samples obtained from a patient such as blood or serum samples, ear swabs, sputum samples, middle ear fluid or even perhaps urine samples may be employed. Furthermore, it is contemplated that such embodiments may have application to non-clinical samples, such as in the titering of antigen or antibody samples, in the selection of hybridomas, and the like.

In related embodiments, the present invention contemplates the preparation of kits that may be employed to detect the presence of HER-2/neu or neu-related proteins or peptides and/or antibodies in a sample. Generally speaking, kits in accordance with the present invention will include a suitable CTL-stimulating peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container means will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

5. ELISAs

ELISAs may be used in conjunction with the invention. In an ELISA assay, proteins or peptides incorporating dgA antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from 2 to 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

6. Epitopic Core Sequences

The present invention is also directed to protein or peptide compositions, free from total cells and other peptides, which comprise a purified protein or peptide which incorporates an epitope that is immunologically cross-reactive with one or more anti-HER-2/neu antibodies.

As used herein, the term "incorporating an epitope(s) that is immunologically cross-reactive with one or more anti-HER-2/neu antibodies" is intended to refer to a peptide or protein antigen which includes a primary, secondary or tertiary structure similar to an epitope located within a HER-2 proto-oncogene polypeptide. The level of similarity will generally be to such a degree that monoclonal or polyclonal antibodies directed against the HER-2 polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of CTL-stimulating immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of 8 to 20 amino acids in length, and more preferably about 8 to about 15 amino acids in length. It is proposed that shorter antigenic CTL-stimulating peptides will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to HER-2/neu and neu-related sequences. These epitopic core sequences are identified herein in particular aspects as hydrophilic regions of the HER-2/neu proto-oncogene polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on transferrin-binding protein antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 9 or 10 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson & Wolf, 1988; Wolf et al., 1988). Computerized peptide sequence analysis programs (e.g., DNAStar Software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

7. Immunoprecipitation

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

8. Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

9. Vaccines

The present invention contemplates vaccines for use in both active and passive immunization embodiments. Immunogenic compositions, proposed to be suitable for use as a vaccine, may be prepared most readily directly from immunogenic CTL-stimulating peptides prepared in a manner disclosed herein. Preferably the antigenic material is extensively dialyzed to remove undesired small molecular weight molecules and/or lyophilized for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4.578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The peptides of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide monooleate (Aracel A) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Patent Nos. 3,791,932; 4,174,384 and 3,949,064, as illustrative of these types of assays.

10. DNA Segments Encoding Novel Peptides

The present invention also concerns DNA segments, that can be isolated from virtually any mammalian source, that are free from total genomic DNA and that encode the novel peptides disclosed herein. DNA segments encoding these peptide species may prove to encode proteins, polypeptides, subunits, functional domains, and the like of HER-2/neu-related or other non-related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding a CTL-stimulating peptide refers to a DNA segment that contains CTL-stimulating coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified CTL-stimulating peptide-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case, a gene encoding CTL-stimulating peptides, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a CTL-stimulating peptide species that includes within its amino acid sequence an amino acid sequence essentially as set forth in any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29.

The term "a sequence essentially as set forth in any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29" means that the sequence substantially corresponds to a portion of the sequence of either SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29 and has relatively few amino acids that are not identical to, or a biologically functional equivalent of, the amino acids of any of these sequences. The term "biologically functional equivalent" is well understood in the art and is further defined in detail herein (for example, see Preferred Embodiments). Accordingly, sequences that have between about 70% and about 80%, or more preferably between about 81% and about 90%, or even more preferably between about 91% and about 99% amino acid sequence identity or functional equivalence to the amino acids of any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29 will be sequences that are "essentially as set forth in any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding either of the peptide sequences disclosed in any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, or that are identical to or complementary to DNA sequences which encode any of the peptides disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, and particularly those DNA segments disclosed in SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63 and SEQ ID NO:64. For example, DNA sequences such as about 14 nucleotides, and that are up to about 1,000, about 500, about 200, about 100, about 50, and about 25 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; and up to and including sequences of about 10,000 nucleotides and the like.

It will also be understood that this invention is not limited to the particular nucleic acid sequences which encode peptides of the present invention, or which encode the amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, including those DNA sequences which are particularly disclosed in SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63 and SEQ ID NO:64. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a CTL-stimulating peptide in its natural environment. Such promoters may include promoters normally associated with other genes, and/or promoters isolated from any bacterial, viral, eukaryotic, or mammalian cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of CTL-stimulating peptides or epitopic core regions, such as may be used to generate anti-peptide antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful.

In addition to their use in directing the expression of CTL-stimulating peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment any of SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64 will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to peptide-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to DNA sequences of any of SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 nucleotides, but larger contiguous complementarity stretches may be used, according to the length complementary sequences one wishes to detect.

The use of a hybridization probe of about 10–14 nucleotides in length allows the formation of a duplex molecule that is both stable and selective. Molecules having contiguous complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of 50° C. to 70° C. Such selective conditions tolerate little, if any, mismatch between the probe and the template or target strand, and would be particularly suitable for isolating CTL-stimulating peptide-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1993; Segal 1976; Proskop, 1991; and Kuby, 1991, are particularly relevant.

Of course, for some applications, for example, where one desires to prepare mutants employing a mutant primer strand hybridized to an underlying template or where one seeks to isolate CTL-stimulating peptide-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

11. Biological Functional Equivalents Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

12. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

13. Monoclonal Antibody Generation

Means for preparing and characterizing antibodies are well known in the art (See, e.g., Antibodies: A Laboratory Manual, Cold Spring Harbor Laboratory, 1988; incorporated herein by reference).

The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified LTBP-3 protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71–74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immuno-binding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

OLIGOPEPTIDE INDUCTION OF A CYTOTOXIC T LYMPHOCYTE RESPONSE TO HER-2/neu PROTO-ONCOGENE IN VITRO

A. MATERIALS AND METHODS

1. Peptides

HER-2 peptides were prepared by the Synthetic Antigen Laboratory of M.D. Anderson Cancer Center (Houston, Tex.) using Merrifield's solid-phase system and a peptide synthesizer (Ioannides et al., 1993). All reagents were of high purity (>99%) and obtained from Millipore Corporation. Eluted peptides were transferred in aqueous solution by passing over Sephadex G-25 columns and lyophilized. Crude synthetic peptides were separated by reverse-phase HPLC. Identity and purity of the final materials were established by amino acid analysis. Purification yielded single peaks by analytical HPLC and the purity of peptides used in these studies was ≧97%.

2. Immunofluorescence mAbs to CD3 (OKT3-FITC), CD4 (OKT4-FITC), and CD8 (OKT8-FITC) were obtained from Ortho Diagnostic (Ortho, Raitan, N.J.); mAb W6/32 (anti-HLA, -A, -B, -C) was from Dako (Dako-Dakopatts, Denmark); and mAb Leu1 1a (anti CD16) was obtained from Beckton-Dickinson (Mountain View, Calif.). mAb BB7.2 and MA2.1 (anti-HLA-A2)-producing clones were from ATCC, mAb Ab2 against HER-2/neu was obtained from Oncogene Science (Manhasset, N.Y.). Immunofluorescence studies were performed as described (Ioannides et al., 1993).

3. Cells and Cell Lines Tumor lines and leukocytes of the donors of ovarian malignant ascites were phenotyped for HLA-A, B, and C antigens by the blood bank at M.D. Anderson Cancer Center, Leukocytes of PBMC donors used as responder cells (HLA-A, B, C) were typed at the Histocompatibility Laboratory of the Methodist Hospital (Houston, Tex.). The HLA types of the donors are presented in Table 2. Expression of HLA-A2 on ovarian tumors, fibroblasts, and EBV-B cell lines (HLA-A2 transfectants) was confirmed by immunofluorescence using culture supernatant from mAb MA2.1 (Ioannides et al., 1993).

C1R:A2, C1R:A1, and C1R:A3 cells express transfected genomic clones of HLA-A2.1, HLA-A1, and HLA-A3. These cells were obtained from Dr. William E. Biddison, National Institute of Neurological Disorders, Bethesda, Md. C1R (Class I reduced) is a mutant cell line that does not express HLA-A2 (Bednarek et al., 1991; Gammon et al., 1992). These cells were maintained in complete RPMI 1640 medium containing 100 µg/ml L-glutamine, 40 µg/ml gentamicin, and 10% fetal calf serum (FCS) (RPMI-FCS). Ovarian tumors and lines of known HLA phenotype used in these studies were: SKOV3 (HLA-A3, 28, B18, 35, Cw5), OVA-1 (HLA-A1, 24, B8, 35, Cw4), OVA-14 (HLA-A2, 30, B14, 44, Cw2.8), OVA-16 (A2, 19 B8, 35), OVA-24 (HLA-A2, 24, B8, 51, Cw2, 7), and (VA-31 (HLA-A11, -, B60, 62, Cw3). Additional targets used in this study were the EBV-B cell line XxCr (HLA-A2, -, B7, 8, Cw7) and the breast carcinoma line SKBr3 (HLA-A11, -, B18, 40, Bw22). SKBr3 overexpressing HER-2 was obtained from Dr. Mien Chie-Hung, Department of Tumor Biology, M.D. Anderson Cancer Center.

TABLE 2

HLA TYPING OF LYMPHOCYTE DONORS

| No. | Donor number | HLA type | | |
|---|---|---|---|---|
| | | A | B | C |
| 1. | 30 | 2, 33 | 14, 35 | w4 |
| 2. | 41 | 1, 2 | 8, — | w7 |
| 3. | 51 | 1, 2 | 8, — | w7 |
| 4. | 46 | 2, 2 | 18, 60 | w3 |
| 5. | 86 | 2, 2 | 18, 61 | w3 |
| 6. | 14 | 32, — | 41, 51 | N.D.[a] |
| 7. | 15 | 1, 32 | 8, 35 | w4, w7 |

[a]Not determined.

Ovarian tumors were separated from TIL/TAL by centrifugation over Ficoll-Hypaque gradients, as previously described (Ioannides et al., 1991), and stored frozen in aliquots in liquid nitrogen until used. Ovarian tumor lines were maintained in culture in L-15 medium (Gibco, Life Technologies, Grand Island, N.Y.) supplemented with 10% FCS and 20 µg/ml gentamicin. Ovarian CTL-TAL lines autologous with OVA-1, OVA-14, OVA-16, and OVA-31 have been generated as described from lymphocytes infiltrating malignant ascites (TAL) by coculture of tumors with TAL in RPMI-FCS in the presence of 25–50 U/ml of IL-2 (Cetus, Emeryville, Calif.) and 250 U/ml of tumor necrosis factor-α (TNF-α) (Genentech, San Francisco, Calif.) (Ioannides et al., 1991).

4. Transfection of Ovarian Tumor Line SKOV3 with HLA-A2

The HLA-A2 expression vector RSV.5-neo containing HLA-A2.1 full-length cDNA was provided by Drs. Richard V. Turner and William E. Biddison. The RSV.5-neo expression vector is a derivative of RSV.3 (Jacobson et al., 1989). The SKOV3 cell line was cloned by stringent limiting dilution (Ioannides et al., 1993), and individual clones were transfected with the plasmid using the Lipofectin reagent and procedure (Gibco-BRL, Gaithersburg, Md.) as described by the manufacturer. Transfectants were selected in culture with 800 µg/ml of G418 (Sigma Chemical Co., St. Louis, Mo.). Surface expression of HLA-A2 was determined by immunofluorescence with MA 2.1 mAb as described (Ioannides et al., 1993). Several clones that expressed high levels of HLA-A2 such as 2B6 (SKVO3.A2) were selected for cytotoxicity studies.

5. Cytotoxicity Assays

Tumor cells and fibroblasts were labeled with 200 µCi of $^{51}$Cr (Na$^{51}$CrO$_4$; Amersham, Arlington Heights, Ill.) for 90 min at 37° C. (Ioannides et al., 1991). Lymphoblastoid cells and HLA-A2 transfectants were labeled overnight in RPMI-FCS, then washed three times and incubated with effector cells in RPMI-FCS in an incubator with 5%. $CO_2$ (Bednarek et al., 1991; Gammon et al., 1992). When peptide recognition was determined, targets were incubated with 25 µM of peptides overnight during $^{51}Cr$ labeling or with 10 µM peptide for 2 h at 37° C. in RPMI-FCS then washed three times before being incubated with effector cells. Separate controls for spontaneous and total lysis were made for each peptide-pulsed target (Ioannides et al., 1991; Bednarek et al., 1991; Gammon et al., 1992). After 4–5 h, 100 µl of supernatant was collected and counted. To determine maximum lysis in 20-h assays, plates were left undisturbed in the incubator and the supernatant was collected after overnight incubation. For cold target inhibition studies, C1R:A2 cells were preincubated with HER-2 or control peptides overnight, then washed and admixed with $^{51}Cr$-labeled targets at 2:1 and 6:1 (cold:hot targets) ratios. Percentage lysis was calculated from the formula: 100×[(E–S)/(T–S)], where E is experimental release, S is release in the absence of CTL, and T is release in 2 M HCl.

6. Generation of In Vitro HER-2 Peptide-Reactive CTL

CTL cultures reacting with HER-2 peptides were generated following procedures described for in vitro induction of influenza matrix and tum⁻ peptide-specific CTL (Bednarek et al., 1991; Gammon et al., 1992; Alexander et al., 1991) with several modifications. In brief, PBMC from HLA-A2⁺ and HLA-A2⁻ donors were separated by Ficoll-Hypaque™ gradient centrifugation. PBMC (5–10×10⁶) were washed, resuspended in a final volume of 100–250 µl in PBS, and incubated with the stimulating peptide for 90 min at 37° C. The final concentration of the stimulating peptide ranged between 5 and 50×10⁻⁶ M. Afterwards, cells were irradiated (4000 rad), washed, and plated in wells of 24-well plates (Costar, Cambridge, Mass.) in 2.0 ml at a final concentration of 0.5–1.0×10⁶ cells/ml. As responding cells, autologous PBMC were added at a final concentration of 1.0–1.5×10⁶/ml. Sequences of HER-2 peptide analogs used for stimulation or specificity determination are presented in Table 3.

Cultures were initiated in RPMI 1640 medium containing 100 µg/ml L-glutamine, 40 µg/ml gentamycin, and 5% heat-inactivated and sterile-filtered human AB plasma (RPMI-HS). After 3 days, 5 U of IL-2 (Cetus) was added in each well. One unit of IL-2 (Cetus) equals 6 IU of IL-2 (Ioannides et al., 1991). After 2 additional days one-third of the medium from each well was replaced with an equal volume of RPMI-HS containing 15 U/ml of IL-2. Four days later, cells were removed from cultures, washed, and restimulated either with irradiated fresh autologous PBMC or C1R:A2 cells pulsed with HER-2 additional days the expanding cultures were restimulated with peptides following the procedures described above. Five to 6 days after the second stimulation and 7 to 8 days after the third and subsequent stimulations, cultures were tested for cytotoxic activity against C1R:A2 cells pre-pulsed with HER-2 peptides and unrelated control peptides containing HLA-A2 anchor motifs.

Cultures that showed higher lysis of targets pulsed with HER-2 peptides than control peptides were maintained for further studies. These cultures were propagated and expanded by periodic cycles of restimulation with peptide-pulsed fresh autologous PBMC as antigen-presenting cells. After the fourth stimulation cells were gradually adapted to growth in RPMI-FCS by replacing 25% of the culture medium every 3 days with RPMI-FCS over a period of 2 weeks. CD3⁺CD8⁺CD4⁻ cells were isolated from bulk CTL cultures by positive selection on anti-CD8 mAb-coated culture flasks (AIS Micro CELLector, Applied Immune Sciences, Menlo Park, Calif.) as described (Letessier et al., 1991). Isolated CD8⁺ cells were restimulated with HER-2 peptide-pulsed PBMC, either autologous or in some instances allogeneic that matched only HLA-A2 with the responding cells.

TABLE 3

SEQUENCES OF PEPTIDES

| Peptide[a] | | | | | | | Sequence | | | | | | | | SEQ ID NO: |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | |
| 1. C43 | R | F | R | E | L | V | S | E | F | S | R | M | A | R | 65 |
| 2. C85 | | | | E | L | V | S | E | F | S | R | M | | | 7 |
| 3. C84 | | | | E | L | V | S | E | F | S | R | V | | | 6 |
| 4. C44 | R | F | R | E | L | I | I | E | F | S | R | M | A | R | 66 |
| 5. D132 | Muc-1:16-1 | | | S | L | A | D | P | A | H | G | V | | | 67 |
| 6. D125 | Muc-1:8-17 | | | G | L | T | S | A | P | D | T | R | V | | 68 |

[a]Peptides 1–4 are analogs of HER-2:968–981 (C43 and C44) and 971–979 (C85 and C84). The substitution VS→II in C44 is found in the equivalent sequence of the epidermal growth factor receptor. D132 is an analog of the Muc-1 core peptide where L(P2) and D(P4) substitute for Thr and Pro, respectively, to create a P2 anchor and a hydrophilic residue at P4, respectively. In the D125 peptide, also an analog of the muc-1 core peptide, L(P2) and V(P10) also substitute for Val and Pro, respectively. Substituted amino acids are in bold and underlined.

B. RESULTS

1. Generation of In Vitro HER-2 Peptide Reacting CTLs

To define conditions for in vitro CTL induction by stimulation with HER-2 peptides of PBMC from healthy volunteers, two synthetic peptides were used for priming: (1) C43 (HER-2:968–981)=RFRELVSEFSRMAR (SEQ ID NO:31), which contains as HLA-A2 anchors Leu(972) at P2 and Met(979) at P9, includes two Rothbard epitope motifs ELVS and RMAR and most of the amphiphilic area 968–984; and (2) C84 (HER-2:971–979(Val))=ELVSEFSRV (SEQ ID NO:6) where Met(P9) has been substituted by Val because Val is the dominant anchor residue at P9 and although it does not contact the TCR (Malden et al., 1993), it stabilizes the HLA-A2-HER-2 peptide complex. Leu and Met were also found in CTL epitopes at P9, as indicated by sequence information (Parker et al., 1992). These peptides were selected because of our previous observations that tumor reacting CTL-TAL isolated from lymphocytes infiltrating ovarian malignant ascites can recognize synthetic peptides derived from the highly amphiphilic area HER-2:968–984 on HLA-A2+ targets (Ioannides et al., 1993). All cultures were initiated in RPMI-HS to avoid induction of T-cells reactive with determinants on FCS proteins. In contrast, cytotoxicity assays were performed in RPMI-FCS to minimize interferences from recognition by CTL of human proteins (Wolfel et al., 1993).

Figure 1B:
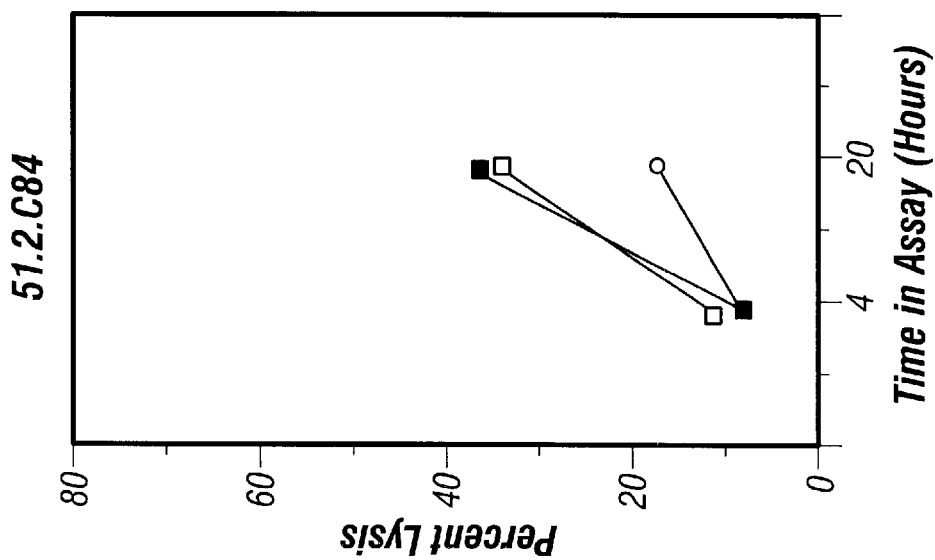
FIG. 1B. Lysis of C1R:A2 cells after sensitization with peptides C43 (HER-2:968–981) (■) and C84 (HER-2:921–979(Val) (□) or in the absence of exogenously added peptides (0) by CTL cultures induced in vitro with C43 and C84 peptides. Headings indicate: donor number (e.g., 51), number of stimulations with peptide (e.g., 2×/3×), and the peptide used for stimulation. Shown is the donor 51 PBMC were stimulated two times with the C84 peptide and tested 3 weeks after.
Figure 1A:
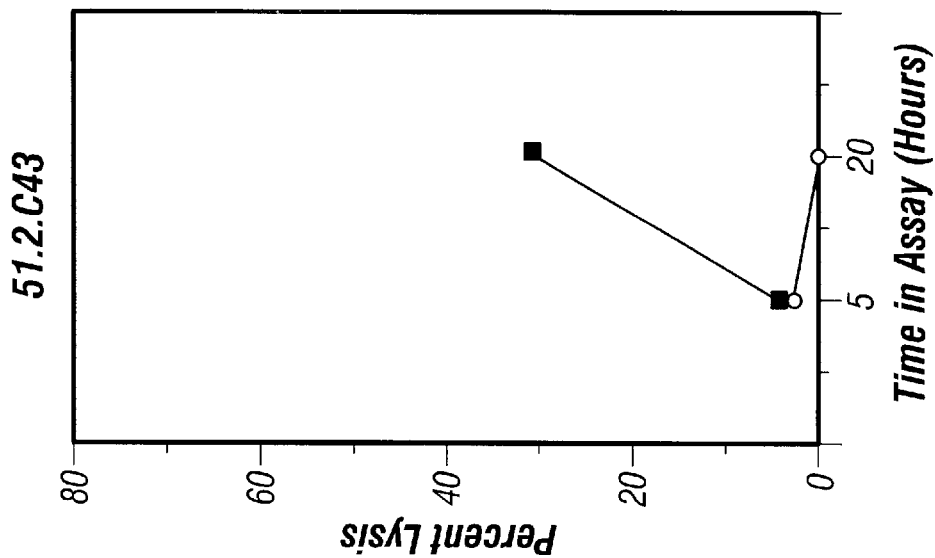
FIG. 1A. Lysis of C1R:A2 cells after sensitization with peptides C43 (HER-2:968–981) (■) and C84 (HER-2:921–979(Val) (□) or in the absence of exogenously added peptides (0) by CTL cultures induced in vitro with C43 and C84 peptides. Headings indicate: donor number (e.g., 51), number of stimulations with peptide (e.g., 2×/3×), and the peptide used for stimulation. Donor 51 PBMC were tested 3 weeks after the second stimulation with the C43 peptide (total 5 weeks in culture). The studies were performed in triplicate. The differences between individual determinations were less than 10%. The differences between HER-2 peptide and control targets recognition are significant in 20-hr assays (P<0.003 for C43 and P<0.027 for C84) and are not significant (P<0.10) in 4-hr assays. The effector to target ratio was 10:1.

The ability of PBMC cultures to recognize peptides used for priming was determined by measuring the lysis of peptide-pulsed C1R:A2 cells. Three out of five individual cultures tested lysed C1R:A2 targets pulsed with C43, C84, or both. Results with two representative donors (No. 41 and No. 51) are shown in FIG. 1. It should be mentioned that these two donors were siblings and had identical HLA phenotype. A common feature of C43- and C84-induced cultures was that they showed minimal lysis of C1R:A2 cells in 4-h cytotoxicity assays but significant differences were observed between lysis of peptide pulsed and control C1R:A2 targets in 20-h assays at 2–3 weeks after stimulation. When cytotoxicity was determined early (1 week after stimulation), in certain instances, they showed high background lysis. Interestingly, all cultures stimulated with the C84 peptide showed similar levels of lysis of either C43-or C84-pulsed targets in 20-h cytotoxicity assays (FIG. 1A, FIG. 1B, FIG. 1C, FIG. 2A, and FIG. 2B).

Figures 2A, 2B:
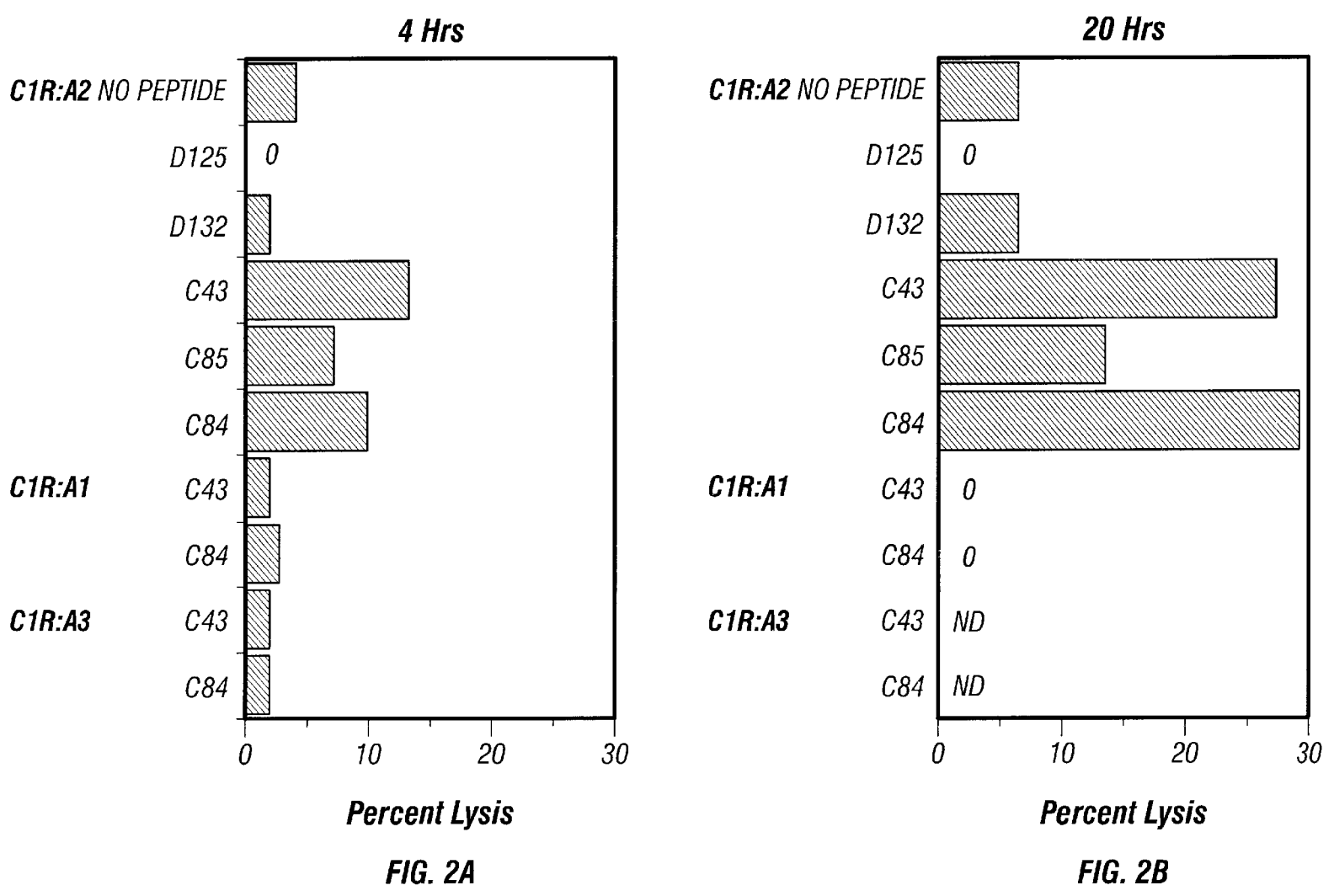

HER-2 peptide-stimulated PBMC cultures tend to lose specificity over time and that the numbers of CD8+ cells tend to decrease, due to overgrowth of CD4+ cells. CD8+ cells were isolated from bulk CTL cultures from donor 41 by positive selection on anti-CD8 mAb-coated plates. The resulting cells were 100% CD3+, 97% CD8+, and 1% CD4+. Separated CD8+ cells were propagated in culture by repeated stimulations with C43 and C84 peptide-pulsed PBMC and expanded in medium containing 15–25 U/ml of IL-2 for more than 6 months. The 41.CD8+ CTL line recognized both C43 and C84 peptides and at a much lesser extent, control D125 and D132 peptides. These peptides contain HLA-A2 anchors introduced by us but differ in sequence form HER-2 peptides (Table 3). The absence of HLA-A2 anchors in the natural sequence of D125 and D132 suggests that they are not presented to corresponding CTL in humans. The sequences of D125 and D132 were chosen from Muc-1 core sequence (Gendler et al., 1988). When C43 and C84 peptides were preincubated with C1R:A1 cells (HLA-A1 transfectants which expressed only HLA-A1), 41.CD8+ CTL failed to elicit a higher lysis of peptide pulsed than of control targets. Similar results were observed with HLA-A3 transfectants (FIG. 2A and FIG. 2B). These results suggested that 41.CD8+ CTL line is peptide Ag specific. Similar results were obtained with PBMC from donor 30 stimulated with C43/C84 peptides. HLA-A2+ transfectants did not cross-present C43/C85/C84 to HLA-A2− CTL from donors 14 and 15 (Table 3) induced with the same peptides. This may suggest that recognition of C43/C84 is HLA-A2 restricted. C43/C85/C84 lack anchor residues for HLA-A1:E(P3), P(P4) and Y(P9); HLA-B8:K(P3), R(P5) and L(P9) (Dibrino et al., 1994), as well as for HLA-B35:Pro (P2) and Tyr(P9) (Hill et al., 1992).

Figure 3C:
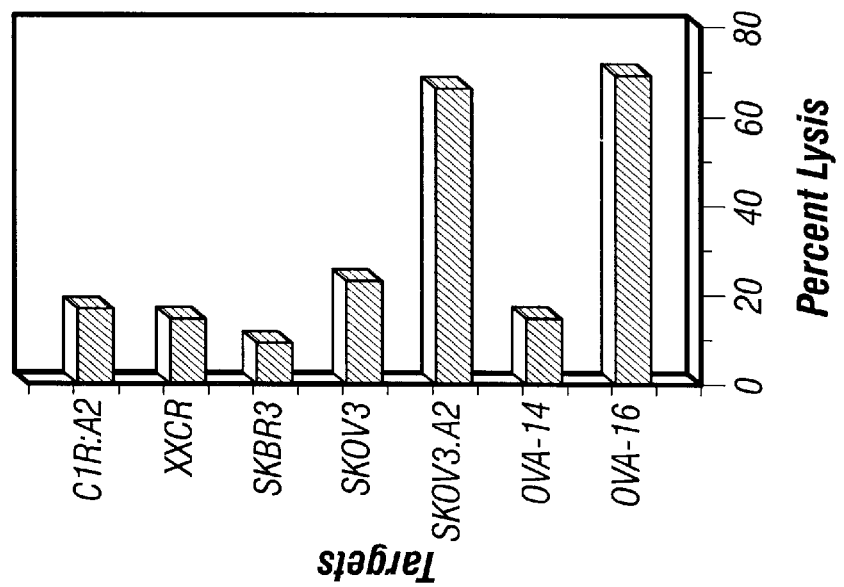
FIG. 3C. Lysis by 41.CD8+ CTL of HLA-A2+ HER-2$^{high}$, HER-2$^{low}$ ovarian tumors and HLA-A3+ HER-2$^{high}$ (SKOV3) ovarian and HLA-A11+ HER-2$^{high}$ (SKBr3) breast tumor lines. C1R:A2 and XX Cr cells were negative control targets.
Figure 3B:
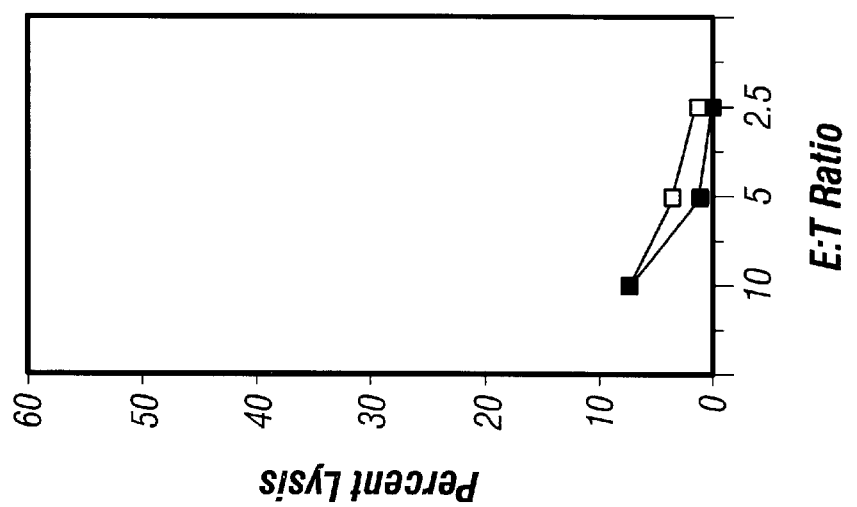
FIG. 3B. Lysis of fresh isolated ovarian tumor K562 cells by the donor 41 CD8+ cell line. Target lysis was determined in 5-hr (□) and 20-hr (■) assays in the same study against both targets.
Figure 3A:
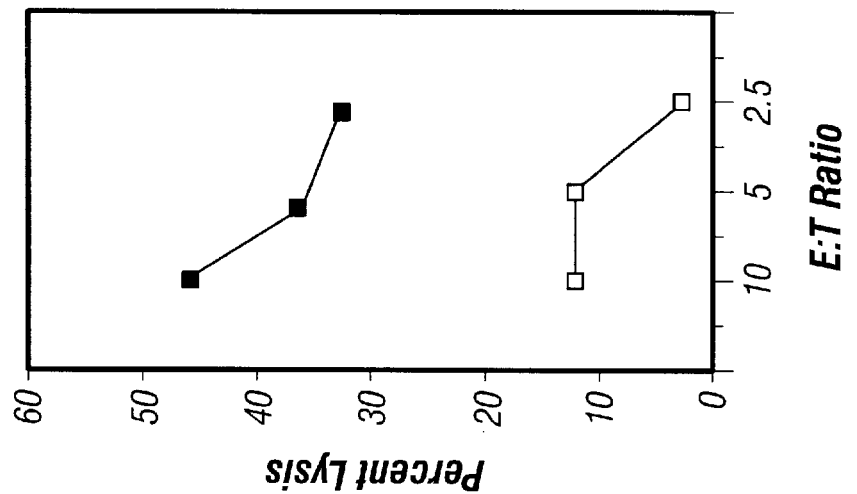
FIG. 3A. Lysis of fresh isolated ovarian tumor OVA-16 (HLA-A2+, HER-2$^{high}$) cells by the donor 41 CD8+ cell line. Target lysis was determined in 5-hr (□) and 20-hr (■) assays in the same study against both targets.

2. HER-2 Peptide-induced CD8+ Cells can Lyse Ovarian Tumors Overexpressing HER-2 Proto-oncogene In vitro peptide-induced CTL cultures can recognize HER-2 peptides used as immunogen. The major question with respect to the specificity of in vitro-induced CTL is whether they can specifically lyse targets endogenously expressing the antigen of interest. To address this question, the ability of HER-2 peptide-stimulated CTL to lyse ovarian tumors overexpressing HER-2 protein was investigated. The ability of 41.CD8+ CTL line to lyse an ovarian tumor (OVA-16) overexpressing HER-2 was tested using NK-sensitive targets as lysability controls. OVA-16 tumor shared HLA-A2 with donor 41 effectors (Table 2). The ability of 41.CD8+ effectors to lyse OVA-16 was determined at 4 and 20 h. The results are shown in FIG. 3A and FIG. 3B. As expected from the results presented in FIG. 1A, FIG. 1B, FIG. 1C, FIG. 2A and FIG. 2B, lysis of OVA-16 by 41.CD8+ effectors in 4-h assays was low, although higher than K562. In 20-h cytotoxicity assays, lysis of OVA-16 was significantly higher than K562 cells.

To determine whether susceptibility of ovarian tumors to lysis correlates with levels of HER-2 protein expression on tumor, the ability of the 41.CD8+ CTL line to lyse two HLA-2+ fresh isolated ovarian tumors OVA-16 and OVA-14 was tested. The results are presented in FIG. 3C. Both shared only HLA-A2 with the donor 41, but they differed at the levels of expression of HER-2. Immunofluorescence staining with the anti-HER-2-specific mAb showed 77.5% HER-2+ cells with a mean fluorescence intensity (MFI) of 28.67 for OVA-16 and 17.4% HER-2+ cells with a MFI of 6.2 for OVA-14. They were designated as HER-2$^{high}$ and HER-2$^{low}$ respectively. The control HLA-A target, ovarian tumor line SKOV3 (99% HER-2+) was also designated as HER-2$^{high}$.

The 41.CD8+ line showed significantly higher lysis of HER-2$^{high}$ than HER-2$^{low}$ targets, suggesting that lysis of HER-2 expressing ovarian tumors may be dependent on Ag density. Lysis of the OVA-14 tumor was similar to that of control XxCr and C1R:A2 cells (HLA-A2+, HER-2−) and SKBr3 (HLA-A2−, HER-2$^{high}$). The SKOV3 tumor (HLA-A2−, HLA-A3+, HER-2$^{high}$) was lysed at levels comparable with control lines, suggesting that HER-2 recognition requires presentation by HLA-A2, because SKOV3.A2 targets were recognized. Both OVA-14 and OVA-16 expressed comparable levels of HLA-A2 antigens on the surface as determined by immunofluorescence with MA2.1 mAb (92.1% HLA-A2 positive cells and 49.0 mean fluorescence for OVA-14 and 85.3% HLA-A2 positive cells and 42.0 mean fluorescence for OVA-16, respectively). In separate studies, OVA-16, OVA-14, and SKOV3 tumors were efficiently lysed by LAK cells, suggesting that there were no major differences in their lysability by cytolytic effectors.

It is unlikely that tumor killing by 41.CD8+ CTL reflects LAK type activity. LAK cells lyse K562 with higher efficiency than they lyse human tumors (Grimm et al., 1982). Also, both C1R:A2 and SkOV3.A2 were transfected with the same HLA-A2 plasmid expression vector. Therefore, lysis of SKOV3.A2 but not of C1R:A2 suggests that 41.CD8+ CTL are not only HLA-A2 reactive but also Ag reactive. In separate studies, LAK cells lysed effectively both C1R:A2 and T2 cells. This lysis was not affected by C43/C84 or mutated peptides based on this sequence. These results show that HER-2 peptide-induced CD8+ cells from human PBMC can recognize targets endogenously expressing HER-2 protein.

Figure 4B:
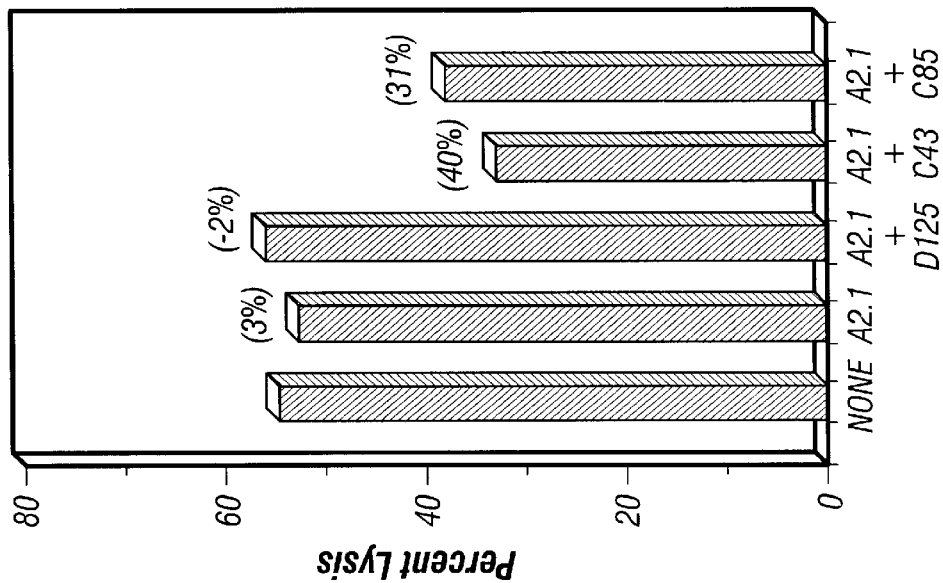
FIG. 4B. Target specificity of the 41.CD8+ CTL were tested for the ability to lyse $^{51}$Cr-labeled OVA-16 at an E:T ratio of 10:1. C1R:A2 cells (A2.1) were incubated with synthetic peptides (D125, C43, C85), washed, and used in cold target inhibition studies at a cold:hot ratio of 2:1. Cytotoxicity studies were performed for 20 hr. Results represent the mean of three determinations. The variability between samples was less than 10%. The differences between determination are statistically significant (P<0.03) as determined by Student's t test. Percentage inhibition is indicated in parentheses.
Figure 4A:
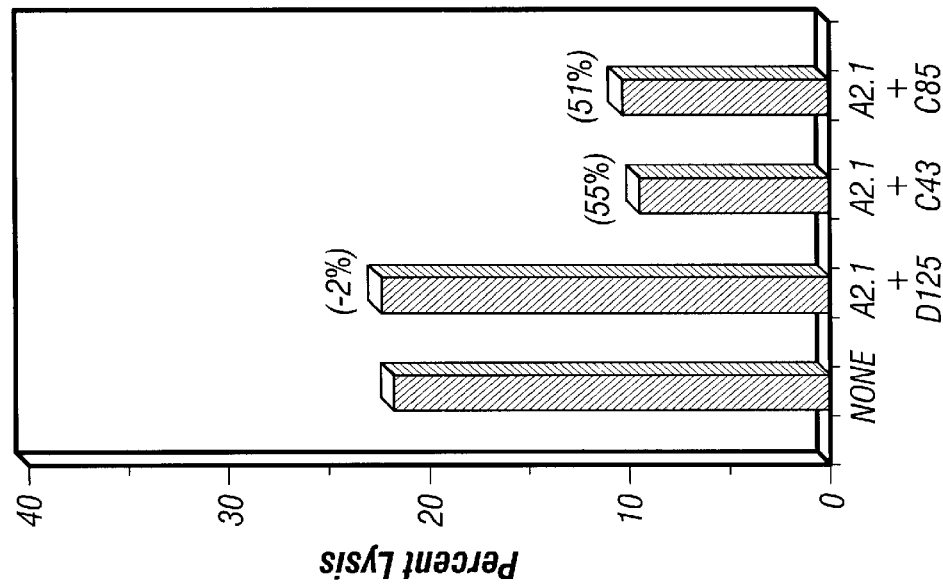
FIG. 4A. Target specificity of the 41.CD8+ CTL were tested for the ability to lyse 5$^1$Cr-labeled OVA-16 at an E:T ratio of 10:1. C1R:A2 cells (A2.1) were incubated with synthetic peptides (D125, C43, C85), washed, and used in cold target inhibition studies at a cold:hot ratio of 2:1. Cytotoxicity studies were performed for 5 hr. Results represent the mean of three determinations. The variability between samples was less than 10%. The differences between determination are statistically significant (P<0.03) as determined by Student's t test. Percentage inhibition is indicated in parentheses.

To confirm that the 41.CD8+ CTL line recognizes epitopes on HER-2$^{high}$ tumors contained on peptides used for stimulation, cold target inhibition studies were performed. In an attempt to inhibit lysis of the OVA-16 tumor by 41.CD8+ CTL with either C43- or C85-(the wild-type HER-2 peptide 971–979) pulsed C1R:A2 cells were used with C1R:A2 cells alone or pulsed with the D125 peptide as controls. The results are shown in FIG. 4A and FIG. 4B. Inhibition of OVA-16 lysis by the 41.CD8+ line was observed in both 4- and 20-h assays. C43- and C85-pulsed C1R:A2 cells but not specificity controls, C1R:A2 cells alone or pulsed with the D125 peptide,inhibited the lysis of the OVA-16 tumor. As expected, levels of lysis were lower in 4-h versus 2-h assays. Increasing the cold:hot ratio to 6:1 did not significantly increase the inhibitory effects of the HER-2 peptide-pulsed C1R:A2. That highly specific, but incomplete, inhibition was observed here and in other human CTL systems (Jerome et al., 1993) reflect low Ag (peptide) density on targets use for inhibition or an increase in background nonspecific lysis as observed in FIG. 3C.

These peptides were recognized by autologous tumor reactive CTL-TA1, suggesting the presence on the tumor of similar or cross-reactive CTL epitopes (Ioannides et al., 1993). To address whether these peptides interfere with tumor lysis by autologous tumor reactive CTL-TAL in HLA-A2$^-$ systems, the lysis of OVA-1, HER-2$^{high}$ (HLA-A1, 24, B8, 35, Cw4) and OVA-31, HER-2$^{high}$ was determined by pre-pulsing with either C43 or as a control, C44 peptide (VS→II). Target lysis by CTL-1 was: OVA-1 (68%), K562 (18%), OVA-1 plus C43 (37%), and OVA-1 plus C44 (51%). C43 significantly inhibited by 45% lysis of OVA-1 by CTL-1, while less inhibition (25%) was observed with C44. However, C43 and C44 had no effect on lysis of OVA-31 by CTL-31. This suggested that these peptides can bind certain MHC Class I heavy chains other than HLA-A2 and can interfere with lysis of certain HLA-A2$^-$ tumors by autologous CTLs.

Therefore CD8$^+$ CTL lines can be induced in vitro with HER-2 peptide analogs and lyse ovarian tumors overexpressing HER-2. It is also likely that a T-cell epitope with a sequence similar or cross-reacting with peptide analogs from the area HER-2:968–981 is associated with HLA-A2 on the tumor cell surface.

C. DISCUSSION

Evidence has been presented showing that human PBMC from healthy volunteers can be primed in vitro with HER-2 peptide analogs to develop lymphocyte cultures with Ag-specific CTL activity. A CD8$^+$ CTL line developed from bulk cultures recognized not only peptides used as immunogen but also ovarian tumors endogenously expressing HER-2. Peptide-induced CD8$^+$ CTL lysed targets endogenously expressing HER-2 but not K562 cells, an ovarian tumor expressing low levels of HER-2. Furthermore, based on the ability of C1R:A2 cells pulsed with C43, C85, or C84 to inhibit HER-2$^{high}$ tumor lysis compared with the inability of C1R:A2 cells alone or pulsed with D125 to mediate the same inhibition, the findings demonstrate that HER-2 peptide-induced CD8$^+$ CTL recognizes similar or cross-reactive epitopes on tumors expressing HER-2. At similar levels of HLA-A2 expression efficiency of tumor lysis was dependent on the levels of HER-2 expression.

The weak lysis observed in 4-hr assays does not reflect "slow" lysis. Slow lysis rarely achieves target lysis above 50% at E:T ratios of 60:1 in 20- to 24-hr assays (Ratner and Clark, 1993). CTL showed levels of lysis in the range of 60–80% at 10:1 or even 5:1 E:T ratios. One possibility to be considered is that the frequency of HER-2 reactive clones in peptide-induced CTLs is relatively low and they diluted among non-cytotoxic cells. The 41.DD8$^+$ line secreted TNF-A when cocultured overnight with C1R:A2 cells in the presence, but not in the absence, of HER-2 peptides. TNF-A secretion was inhibited by HLA-A2 specific MA2.1 mAb, suggesting that peptide recognition associated with HLA-A2 is needed for lymphokine secretion. With respect to the efficiency of these peptides for target sensitization for maximum lysis this was observed when targets were preincubated with 5 μM peptide for 1 hr or cultured with 25 μM peptide overnight. The amount of peptide bound on HLA-A2$^+$ molecules cannot be estimated, however, by comparing with other reports on human CTL assays performed in the presence of peptide in solution, these CTLs needed 2–3× 10$^2$-fold more peptide for similar levels of target recognition, but in 20-hr assays (Gammon et al., 1992; Schmidt et al., 1991; Kos and Müllbacher, 1992; Stauss et al., 1992; Anderson et al., 1992). This peptide concentration is significantly less than the 10$^7$-fold difference in peptide concentration needed for efficient Ag recognition reported for murine CTL induced in vivo and in vitro by peptides (Schild et al., 1991).

It may be possible that if HLA-A2 acts as a restriction element for specific HER-2 peptides, TCR with high affinity for these natural peptides may be eliminated during thymic selection, leaving only TCR with low affinity (Bowness et al., 1993). The only conservative substitution introduced to strengthen the P9 anchor (Met→Val) had no inhibitory effects in peptide-stimulating ability or CTL specificity. TCR contacts mainly residue in the sequence P4–P7, while P2 and P9 are buried in the HLA-A2 binding pockets (Madden et al., 1993). Of interest, the 14mer peptide C43 had similar sensitizing ability for lysis of targets as the shorter peptide C84. Although it may be possible that activity in C43 is associated with the presence of contaminating peptides at levels lower than the ability of detection, several other possibilities need to be taken in consideration: proteolytic degradation as extracellular processing occurs and the longer peptides are better substrates than shorter than peptides for proteolysis (Sherman et al., 1992). This may also suggest a role for the group RFR and/or the carboxy-terminal R in Ag processing before HLA-A2 binding.

Since targets were always pulsed with the same concentrations of peptides, the kinetics of target recognition may also reflect different effects of factors involved in in vitro priming of T-cells with Ag. It has been previously shown that by increasing both responder cell and Ag (peptide) density, murine Ag-specific CTL can be induced in vitro. These CTL recognized targets which endogenously expressed the Ag of interest (Winter et al., 1991).

The experience with in vitro induction of human CTLs by peptide is limited. Recent reports have shown that Ag-specific CTLs can be induced in vitro using peptide analogs of EBV nuclear antigens (EBNA) (Schmidt et al., 1992), influenza matrix (Bednarek et al., 1991; Gammon et al., 1992), or Plasmodium falciparum pre-erythrocytic stage antigens (Hill et al., 1992). Given the frequency of EBV and influenza infections it is possible that they represented, at least in some instances, secondary CTL responses of in vivo-primed T-cells. Based on molecular mimicry between self and foreign proteins at the three and tetrapeptide levels (Ohno, 1991), it is not unlikely that naturally processed T-cell epitopes from self-proteins may be cross-reactive (Anderson et al., 1992).

Since HER-2 is a self-antigen, HER-2 reactive T-cells may be primed in vivo and non-deletional mechanisms of tolerance in the periphery may render HER-2-primed T-cells anergic or suppressed. However, a recent report demonstrated that Ag-reactive T-cells transferred in Ag-reactive T-cells transferred in Ag tolerant transgenic mice can be recovered, suggesting that tolerance induction in the periphery may not affect primed T-cells and that the lack of auto-reactivity may be because of the low levels of antigen expressed on normal cells (Hu et al., 1993). The HER-2 proto-oncogene product is expressed at low levels in normal cells of origin. Results suggest that in vivo priming to HER-2 epitopes is possible when HER-2 is expressed at 100- to 200-fold higher than normal levels (Ioannides et al., 1993). In contrast with viral infections which essentially turn off the host protein synthesis to favor the expression of virally coded polypeptides, overexpression of HER-2 does not generally inhibit the tumor's protein synthesis. Thus, additional antigens are expected to compete with HER-2 for HLA-A2 binding and presentation to TCR.

PBMC from 5 of 11 healthy HLA-A2$^+$ volunteers tested showed CTL responses to HER-2 peptides used for priming, and CTLs and tumor clones have been developed to identify HER-2 epitopes recognized by tumor reactive CTLs.

EXAMPLE 2

SEQUENCE MOTIFS OF HUMAN HER-2 PROTO-ONCOGENE IMPORTANT FOR PEPTIDE BINDING TO HLA-A2

A. MATERIALS AND METHODS

1. Peptides

HER-2 peptides were synthesized as described in Example 1. The purity of peptides used in these studies was ≧97%.

2. Immunofluorescence mAbs to CD3 (OKT3-FITC), CD4 (OKT4-FITC) and CD8 (OKT8-FITC) were obtained from Ortho Diagnostic (Ortho, Raritan, N.J.), mAb W6/32 (anti-HLA, -A, -B, -C) from Dako (Dako-Dakopatts, Denmark); HLA-A2 reacting mAb BB7.2 and MA2.1 from ATCC. Immunofluorescence studies were performed as described in Example 1.

3. HLA-typing

Leukocytes of the PBMC donors used as responder cells were typed by the Blood Bank at M.D. Anderson Cancer Center. The HLA-types were as follows: donor 20: HLA-A 2, 11, B35, 51, Cw7, donor 25: HLA-A 2, 3, B44, 60; donor 30: HLA-A2, 33 B14, 35, Cw4. Expression of HLA-A2 on HLA-A2 transfectants was confirmed by immunofluorescence using culture supernatant from mAb MA2.1 (Ioannides et al., 1993).

4. Cytotoxicity Assays

Target cells were labeled with $^{51}$Cr (Na$^{51}$CrO$_4$; Amersham, Arlington Heights, Ill.) for 90 min at 37° C. (Ioannides et al., 1991; Ioannides et al., 1991), or overnight in RPMI medium, containing 10% FCS, 100 μg/ml L-glutamine and 40 μg/ml gentamycin (RPMI-FCS), then washed and incubated with the effector cells in complete RPMI-FCS in an incubator with 5% CO$_2$. Targets were incubated either with 25 μM of peptide overnight during labeling, or with 10 μM peptide for 2 h at 37° C. in RPMI-FCS, then washed three times before being incubated with effector cells. Separate controls for spontaneous and total lysis of targets were made for each peptide pulsed target (Ioannides et al., 1993; Fisk et al., 1994; Gammon et al., 1992). After 4–5 h of incubation 100 μl of supernatant were collected and counted. Percent lysis was calculated from the formula: 100×[(E–S)/(T–S)], were E=experimental release, S=release in the absence of CTL, T=release in 2 M HCl.

5. Target Cells and Cell Lines

The human lymphoblastoid cell lines C1R and T2 have been previously described (Gammon et al., 1992; Bednarek et al., 1991; Salter and Creswell, 1986; Anderson et al., 1993). C1R (Class I reduced) is a mutant cell line that does not express HLA-A2, C1R:A2 cells express transfected genomic clones of HLA-A2.1. These cells were obtained from Dr. William E. Biddison (National Institute of Neurological Disorders, Bethesda, Md.). T2 (transport deletion mutant) cells were obtained from Dr. Peter Creswell (Yale University School of Medicine, New Haven, Conn.). C1R:A2 cells were maintained in RPMI-FCS. T2 cells were maintained in Iscove's Modified Dulbecco Medium (IMDM) containing 5% Fetal Calf Serum (IMDM-FCS).

6. Generation of In Vitro HER-2 Peptide-reactive CTL

CTL cultures were generated following the procedures described for in vitro induction of influenza matrix and tum peptide specific CTL (Gammon et al., 1992; Bednarek et al., 1991; Salter and Creswell, 1986) with several modifications. In brief, PBMC from HLA-A2$^+$ donors were separated by Ficoll-Hypaque™ gradient centrifugation. 5–10×10$^6$ PBMC were resuspended in a final volume of 100–250 μl in PBS and incubated with the stimulating peptide at a final concentration between 5–50×10$^{-6}$ M for 90 min at 37° C. Afterwards, cells were irradiated (4000 rad), washed, and plated in wells of 24 well plates (Costar, Cambridge, Mass.) in 2.0 ml at a final concentration of 0.5–1.0×10$^6$ cells/ml. As responders, autologous PBMC were added at a final concentration of 1.0–1.5×10$^6$/ml.

Cultures were initiated in RPMI 1640 medium containing 100 μg/ml L-glutamine, 40 μg/ml gentamycin and 5% heat-inactivated and sterile filtered human AB plasma (RPMI-HS). The use of human serum during stimulation and culture and of FCS during CTL assays was intended to avoid induction of FCS peptide reactive CTLs. After three days, 5 U of IL-2 (Cetus) equals 6 IU of IL-2 (Ioannides et al., 1991). Two days later, one third of the medium was replaced with an equal volume of RPMI-HS containing 15 U/ml of IL-2. Four days later, cells were restimulated with irradiated fresh autologous PBMC pulsed with the same peptides. Three days later, 5 U of IL-2 (Cetus) was added to each well. The expanding cultures were subjected to a second round of restimulation as described above. Six days after the first and second stimulations and seven to eight days after the third stimulation, cultures were tested for cytotoxic activity against C1R:A2 cells pulsed with either stimulating peptides or unrelated control peptides. Control cultures were established without HER-2 peptides, containing the same number of autologous stimulators and responders PBMC.

7. Proliferation Assays

Fresh PBMC from healthy volunteers isolated by Ficoll-Hypaque™ were distributed into 96-well round-bottomed plates (Falcon, Becton-Dickinson) at 2×10$^5$/well in RPMI-FCS. Peptides were added at 50 μg/ml. The studies were performed at least twice using PBMC from the same donor, in quadruplicate. After 5 days, for the last 16 h in culture, wells were pulsed with 1 μCi of [$^3$H]-thymidine ($^3$H-Tdr) and counted. Proliferation was determined as $^3$H-Tdr incorporation and c.p.m. determined in the samples of PBMC cultured with peptides and were divided by c.p.m. determined same cultures in the absence of peptides, to determine the stimulation index (S.I.).

B. RESULTS

1. Selection of Candidate Antigenic Peptides from HER-2 Peptides Predicted by Algorithmic Methods Sequence analysis for the presence of potentially amphiphilic areas revealed a small number (<20) of potential sites capable of forming long amphiphilic α-helices over 3–4 turns (12 residues) in the 1255 residue sequence of HER-2 (Ioannides et al., 1993). A number of shorter sequences have also been identified. Most of these sequences contained Rothbard's epitope motifs (Rothbard and Taylor, 1988). Since the focus was peptides presented by HLA-A2, these regions as well as the entire HER-2 sequence were searched for areas containing the predicted, as well as the alternatively reported, HLA-A2 anchors: i.e. L/M/I/V (P2) and V/L/M/I (P9) (Parmiani, 1993; Bednarek et al., 1991; Parker et al., 1992). Several areas were found to meet all three criteria of selection. These areas are as follows:

(a) HER-2: 968–984, which not only forms a perfect amphiphilic helix but also contains two Rothbard's epitope motifs and a nonapeptide with predicted HLA-A2 anchors. This area has been previously found to be recognized by tumor reactive CTL (Ioannides et al., 1993).

(b) The area HER-2:41–56 contains L(43), L(49) and the group VV(55–56). This corresponds to two overlapping potentially HLA-A2 binding peptides: an octapeptide HER-2:42–49 followed by a nonapeptide HER-2:48–56. The presence of HL and VV groups renders these peptides highly hydrophobic, and consequently they have low solubility in PBS or culture medium. With respect to the sequence HER-2:48–56, the corresponding synthetic peptide (D113) had low solubility in PBS. DMSO up to 50% was used for rapid solubilization. The analogs D114=HER-2:47–56(48H→L) and D115=HER-2:48–56(48H→G) were designed in an attempt to improve solubility and increase the ability of exogenously supplied peptides to bind to HLA-A2. To overcome these problems at least in part, peptides D96=HER-2:4–54 and D97=HER-2:42–51 were synthesized, which, although longer than the minimum HLA-A2 binding peptide, are water-soluble.

(c) The area HER-2:391–411 contains two potentially HLA-A2 binding nonapeptides: HER-2:391–399 (PLQPEQLQV) (SEQ ID NO:12) and HER-2:402–410 (TLEEITGYL) (SEQ ID NO:13). An octapeptide HER-2:396–403 with HLA-A2 anchors at P2 and P8:QLQVFETL (SEQ ID NO:14) is nested in the sequence and overlaps with the carboxy- and amino terminal regions of the HER-2:391–399 and 402–410.

Two other areas containing decapeptides: HER-2:344–353=GLGMEHLREV (SEQ ID NO:15) and HER-2:1089–1098=DLGMGAAKGL (SEQ ID NO:16) both include predicted HLS-A2 anchors but not overlapping or continuous epitopes. Several other areas also show potential amphiphilic sites and include Rothbard's epitope motifs. While these areas do not include HLA-A2 anchor motifs, they may, however, include anchors for other HLA-types.

2. Peptides Identified by the Presence of HLA-A2 Anchors

In addition to the sites identified by the overlap of potentially amphiphilic sites and Rothbard's epitope motifs, a number of peptides can be identified in the sequence of HER-2 by the presence of HLS-A2 anchors at positions 2 and 9. A large number of sites (>35) containing nonapeptides with: dominant, strong or weak P2 and P9 anchors predicted or reported for HLA-A2 (Falk et al., 1991) were found in the HER-2 sequence. The sequences of most of these peptides are presented in Table 4. Additional nonapeptides are found in the Leu and Val rich transmembrane domain (655–675). In addition to nonamers, a large number of octa- and decamers were found in the HER-2 sequence containing L/I/V/M as HLA-A2 anchors. These sequences are not included in Table 4 except in a few cases where octa- and decamers are part of epitope clusters. In addition to clustered potential HLA-A2 binding peptides from the signal (Ioannides et al., 1992; Ioannides et al., 1993; Parmiani, 1993; Slamon et al., 1989; Fisk et al., 1994; Falk et al., 1991; Rothbard and Taylor, 1988; DeLisi and Berzofsky, 1985; Stauss et al., 1992) and transmembrane (655–675) areas, putative HLA-A2 binding peptides are clustered either as continuous or overlapping peptides as follows: 42–91 (two 8- and three 9-mers), 141–179 (three 9-mers), 391–419 (three 9-mers), continued with 423–474 (six 9-mers), 781–807 (three 9-mers and one 10-mer), 828–859 (one 8-mer and four 9-mers).

In certain areas, the last two carboxyterminal residues of a putative HLA-A2 binding peptide overlap with the first two aminoterminal residues of the next peptide because P2 and P9 anchors are the same or similar (L/V). Most of the peptides include Rothbard's epitope motifs. However most of the nonapeptides either do not derive from long amphiphilic areas, or are highly hydrophobic according to their sequence; when their sequence is viewed on axial projection (Edmundson's wheel) (Kaiser and Kezdy, 1984) the majority of the peptides (28/38) show limited segregation of hydrophilic and hydrophobic residues.

Crystallographic analysis of the LSA-A2 peptide complex reveals an additional binding pocket in HLA-A2 accommodating a hydrophobic residue in position 6 and the likelihood that residues in positions 4 and 8 are hydrophilic and oriented upwards (towards TDR) (Saper et al., 1991; Madden et al., 1993). None of the nonapeptides of sequences shown in the Table 4 contains all the additional strong anchors in the positions 4, 6, and 8 identified by Rammensee and collaborators (Falk et al., 1991). However at least 3/17 nonamers contain one additional strong HLA-A2 anchor and 11/18 nonamers contains at least two additional weak HLA-A2 anchors (Table 5). For peptide selection the following groups were considered equivalent: L and I at P2, R and K at Pa, P4, P5 and P8, L and M at P9, either because of

TABLE 4

HER-2/NEU PEPTIDES CONTAINING P2 AND P9 HLA-A2 ANCHORS[a]

| Peptide No. | From Amino Acid Position # | To Amino Acid Position # |
| --- | --- | --- |
| 1 | 5 | 13 |
| 2 | 42 | 49 |
| 3 | 48 | 56 |
| 4 | 76 | 84 |
| 5 | 84 | 91 |
| 6 | 141 | 149 |
| 7 | 160 | 168 |
| 8 | 171 | 179 |
| 9 | 369 | 377 |
| 10 | 391 | 399 |
| 11 | 402 | 410 |
| 12 | 411 | 419 |
| 13 | 423 | 431 |
| 14 | 435 | 443 |
| 15 | 442 | 450 |
| 16 | 447 | 455 |
| 17 | 457 | 465 |
| 18 | 466 | 474 |
| 19 | 596 | 604 |
| 20 | 603 | 611 |
| 21 | 627 | 635 |
| 22 | 650 | 658 |
| 23 | 689 | 697 |
| 24 | 747 | 755 |
| 25 | 781 | 790 |
| 26 | 789 | 797 |
| 27 | 793 | 801 |
| 28 | 799 | 801 |
| 29 | 828 | 836 |
| 30 | 835 | 842 |
| 31 | 838 | 846 |
| 32 | 845 | 853 |
| 33 | 851 | 859 |
| 34 | 883 | 891 |
| 35 | 904 | 912 |
| 36 | 971 | 979 |

TABLE 4-continued

HER-2/NEU PEPTIDES CONTAINING P2 AND
P9 HLA-A2 ANCHORS[a]

| Peptide No. | From Amino Acid Position # | To Amino Acid Position # |
|---|---|---|
| 37 | 986 | 994 |
| 38 | 1172 | 1180 |

[a]Selection of anchors was made from the cDNA sequence of human HER-2/neu (Yamamoto et al., 1986). To accommodate HER-2 peptides that may bind HLA-A2 with low affinity both I and V were accepted at position 2. Based on reported epitopes, I can be tolerated at P2. V binds with much lower affinity to HLA-A2. CTL epitopes containing V at P2 have not been reported yet. CTL epitopes containing M at P9 have been reported (Parker et al., 1992). Although M is tolerated at P2 only octa- and deca-peptides were found containing M (P2) in the HER-2 sequence, and they are not included in this table. For the sequences of each of the motifs, see Fisk et al., 1994b.

structural similarities, or because they have been reported to be part of CTL epitopes (Parker et al., 1992).

Sequence analysis of HLA-A2 bound peptides shows an alternation of hydrophobic and hydrophilic residues. P2 and P3 are generally made of hydrophobic residues, P4 of hydrophilic residues, while the charge and hydropathy of residues in P5–P9 alternate, following in general the pattern: P5 (variable/neutral)—P6 (hydrophobic)—P7 (variable)—P8 (hydrophilic)—P9 (always hydrophobic) (Falk et al., 1991). Although the peptide is bound to HLA in an extended conformation stabilized with hydrogen bonds, the alternation between hydrophobic and hydrophilic residues is in general agreement with Rothbard's epitope motifs and with hypotheses that certain T-cell epitopes are derived from amphiphilic sites.

Examination of the physicochemical properties of HER-2 peptides may assist in predicting which of the peptides shown in Table 4 will bind HLA-A2. However this would not address whether these self-peptides are capable of activating T-cells. To gain insight into these questions, specific areas were targeted: 41–56, 392–411, and 968–984. Each area contains a nonapeptide: 48–56 (D113), 402–410 (D119) and 971–979 (C85). All share Leu as P2 anchor. Peptide 43–56 contains the dominant P9 anchor Val, while 402–410 contains Leu and 971–979 contains Met which are expected to be weak anchors. All share a hydrophilic residue at P4: D97 (Q), D119 (E) and C85 (S). Differences are evident in the residues in the other positions, where only C85 has a strong P8 anchor (R). The sequences of peptides from these regions are shown in the Table 4.

3. Effects of HER-2 Synthetic Analogs on Conformational Epitopes on HLA-A2

To determine whether these peptides and longer analogs affect HLA-A2 conformation as an indication of HLA-A2 binding, the effects of HER-2 peptides on the reactivity of conformationally dependent mAb MA2.1 and BB.7.2 were examined with HLA-A2 of T2 cells. The human cell line T2 has a defect affecting endogenous peptide loading of MHC class I molecules. As a consequence, cell surface expression of HLA-A2 is lower (30–40%) than in normal LBL lines transfected with HLA-A2 (e.g., C1R) but the reactivity of MA2.1 and BB.7.2 mAb is increased when certain HLA-A2 binding peptides are added to the culture medium (Anderson et al., 1993). Although most human MHC class I molecules cannot be induced at the low temperatures used for their murine counterparts because of fundamental structural differences between human and mouse class I (Anderson et al., 1993), the fact that they express few endogenous (mainly signal) peptides (Zweerink et al., 1993) increases the sensitivity of detection of peptide-HLA-A2 interaction.

Figures 5A, 5B, 5C:
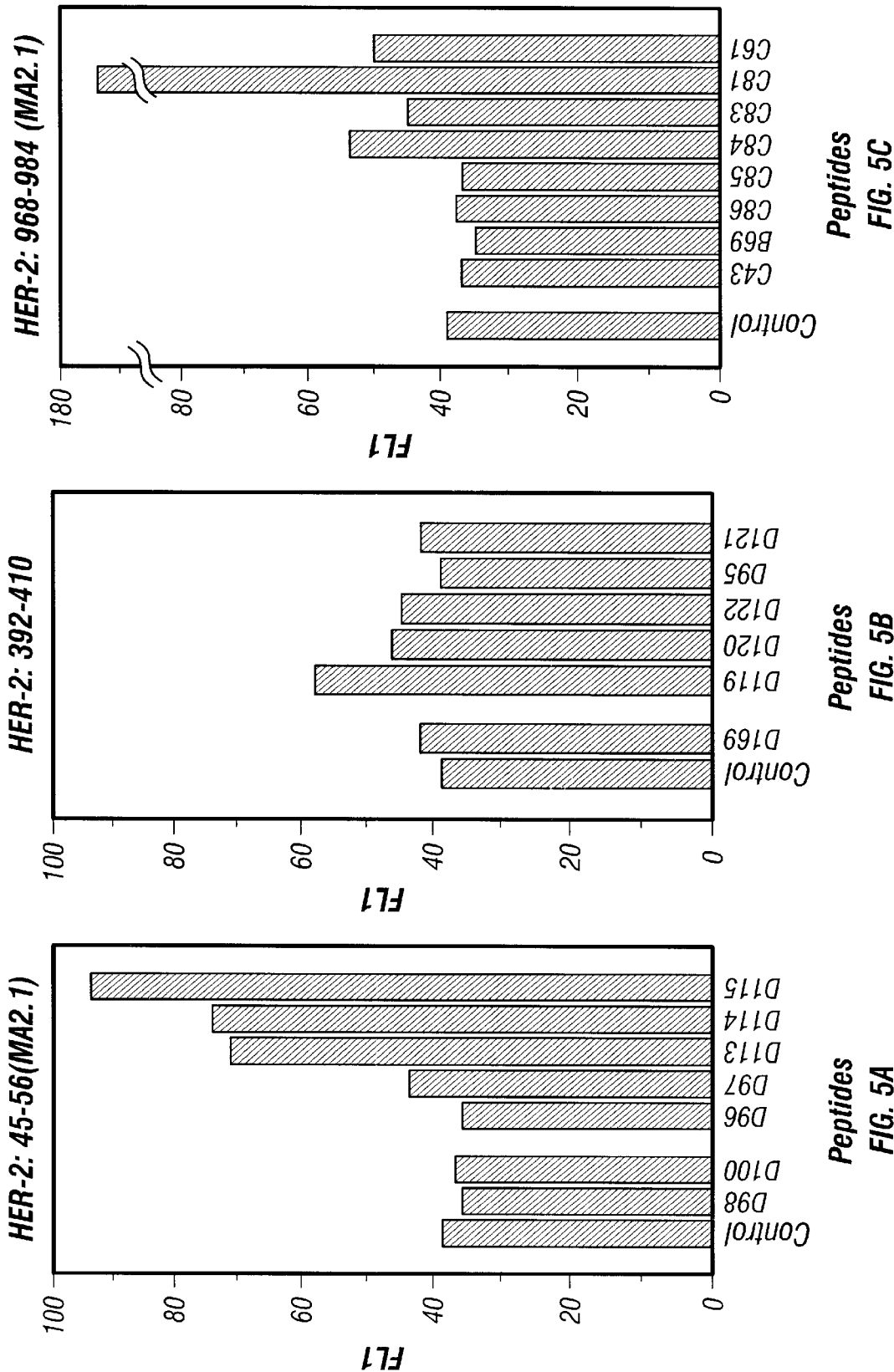
FIG. 5A. Effects of HER-2 peptides on reactivity of MA2.1 mAb with T2 cells. Fluorescence analysis and determination of FL1 were performed as described (Stauss et al., 1992). Peptides were added to T2 cells at 50 μg/ml (final concentration). After overnight culture, in IMDM-FCS, cells were washed and the levels of HLA-A2 expression were determined using HLA-A2 specific mAb. Control indicates that no exogenous peptides was added in the T2 cultures. D98, D160, and D169 are control peptides which do not contain HLA-A2 anchors in correct positions.
FIG. 5B. Effects of HER-2 peptides on reactivity of BB7.2 mAb with T2 cells. Studies were performed as described in the legend to FIG. 5A.
FIG. 5C. Effects of HER-2 peptides on reactivity of MA2.1 mAb with T2 cells. Studies were performed as described in the legend to FIG. 5A.

The results of immunofluorescence studies are presented in FIG. 5A, FIG. 5B, FIG. 5C, and FIG. 5D. The nonapeptide D113 induced a significant increase in FL1. As expected, its analogs D114 and D115 increased FL1 even further (FIG. 5A). However since they have shown low solubility, the study was repeated with peptides dissolved in DMSO. The nonapeptide D113 induced a significant decrease in the reactivity of MA2.1 mAb with HLA-A2. Both D114 and D115 were unable to increase reactivity of MA2.1 with HLA-A2. In contrast, D97 which has identical P1–2 anchors with D113 but nests an octapeptide, D96 which covers the entire area 41–54 with the exception of the VV group (P8–9) of D113 and decapeptide D99= DLGMGAAKGL (HER-2:1089–1098) (SEQ ID NO:5) showed a slight increase in FL1 of T2 cells in comparison with control peptides (D98 and D100) or in the absence of peptide.

TABLE 5

HER-2 PEPTIDES CONTAINING ADDITIONAL
HLA-A2 ANCHORS TO P2 AND P9

| Peptide No. | Position | Sequence | | | | | | | | | No. of Anchors | | SEQ ID NO: |
|---|---|---|---|---|---|---|---|---|---|---|---|---|---|
| | | 1 | 2 | 3 | 4 | 5 | 6 | 7 | 8 | 9 | Strong | Weak | |
| 1 | 48–56 | H | L | Y | Q | G | C | Q | V | V | 2 | 2 | 17 |
| 2 | 76–84 | D | I | Q | E | V | Q | G | Y | V | 3 | 1 | 20 |
| 3 | 141–149 | Q | L | R | S | L | T | E | I | L | 1 | 4 | 21 |
| 4 | 171–179 | D | I | F | H | K | N | N | Q | L | 1 | 3 | 22 |
| 5 | 369–377 | K | I | F | G | S | L | A | F | L | 1 | 6 | 11 |
| 6 | 391–399 | P | L | Q | P | E | Q | L | Q | V | 2 | 1 | 12 |
| 7 | 402–410 | T | L | E | E | I | T | G | Y | L | 2 | 3 | 13 |
| 8 | 411–419 | Y | I | S | A | W | P | D | S | L | 1 | 4 | 23 |
| 9 | 457–465 | S | L | R | E | L | G | S | G | L | 2 | 3 | 24 |
| 10 | 650–658 | P | L | T | S | I | I | S | A | V | 2 | 2 | 25 |
| 11 | 689–697 | R | L | L | Q | E | T | E | L | V | 2 | 2 | 26 |
| 12 | 747–755 | K | I | P | V | A | I | K | V | L | 1 | 4 | 27 |
| 13 | 789–797 | C | L | T | S | T | V | Q | L | V | 3 | 0 | 10 |
| 14 | 828–836 | Q | I | A | K | G | M | S | Y | L | 2 | 3 | 28 |
| 15 | 851–859 | V | L | V | K | S | P | N | H | V | 3 | 1 | 8 |

TABLE 5-continued

HER-2 PEPTIDES CONTAINING ADDITIONAL
HLA-A2 ANCHORS TO P2 AND P9

| Peptide No. | Position | \_ | \_ | \_ | Sequence | \_ | \_ | \_ | \_ | No. of Anchors | | SEQ ID NO: |
|---|---|---|---|---|---|---|---|---|---|---|---|---|
| | | 1 | 2 | 3 | 4 | 5 | 6 | 7 | 8 | 9 | Strong | Weak | |
| 16 | 971–979 | E | L | V | S | E | F | S | R | M | 2 | 1 | 7 |
| 17 | 1172–1180 | T | L | S | P | G | K | N | G | V | 2 | 2 | 29 |

TABLE 6

SEQUENCES OF HER-2 PEPTIDES USED IN THIS STUDY

| Peptide | Position | Sequence | SEQ ID NO: |
|---|---|---|---|
| HER-2 Peptides: | | | |
| D97 | 42–51 | H L D M L R H L Y Q | 30 |
| D96 | 41–54 | T H L D M L R H L Y Q G C Q | 31 |
| D113 | 48–56 | H L Y Q G C Q V V | 17 |
| D114 | 47–56 | R L̲ L Y Q G C Q V V[a] | 18 |
| D115 | 48–56 | G̲ L Y Q G C Q V V | 19 |
| D98 | | N Q E V T A W D G T Q R | 32 |
| D119 | 402–410 | T L E E I T G Y L | 13 |
| D120 | 397–410 | L Q V F E T L E E I T G Y L | 33 |
| D121 | 392–411 | L Q P E Q L Q V F E T L E E I T G Y L Y | 34 |
| D122 | 396–406 | Q L Q V F E T L E E I | 35 |
| D95 | 392–404 | L Q P E Q L Q V F E T L E | 36 |
| C85 | 971–979 | E L V S E F S R M | 7 |
| C86 | 971–981 | E L V S E F S R M A R | 37 |
| C43 | 968–981 | R F R E L V S E F S R M A R | 38 |
| C44 | 968–981 | R F R E L I̲ I̲ E F S R M A R | 39 |
| B69 | 972–984 | L V S E F S R M A R D P Q | 40 |
| C61 | 968–977 | R F R E L V S E F S | 41 |
| D169 | 964–972 | E C R̲ P R̲ F R E L̲[b] | 42 |
| D170 | 968–984 | R F R E L V S | 43 |
| D99 | 1089–1098 | D L G M G A A K G L | 16 |
| D100 | 1086–1098 | F D G D L G M G A A K G L | 45 |
| FBP Peptides: | | | |
| E37 | 25–33 | R I A W A R T E L | 46 |
| E38 | 112–120 | N L G P W I Q Q V | 47 |
| E39 | 191–199 | E I W T H S T K V | 48 |
| E40 | 247–255 | S L A L M L L W L | 49 |
| E41 | 245–253 | L L S L A L M L L | 50 |

[a]Underlined residues represent mutations from the natural sequence of HER-2;
[b]D169 was selected to contain HLA-B8 anchors, shown underlined.

Of peptides from the area 392–410, the analog D119 corresponding to a nonapeptide with dominant P2 and weak P9 anchor showed a significant increase in FL1 over control T2 cells preincubated without peptide. Interestingly, amino-terminal elongation of the peptide (D120) and elongation followed by truncation (D122) increased the FL1 only slightly over the base level. Similarly, a peptide (D121) containing the entire area failed to significantly affect the FL1, suggesting that it is probably not processed by external proteases to shorter fragments of correct length.

The model nonapeptide C85 (=HER-2:971–979) from the third area failed to significantly increase FL1 of T2 cells reacting with MA2.1. C85 contains a dominant P2, a strong P8 and weak P9 anchor. This was also true for longer analogs B69 and C43. To address the question whether this reflects the weakness of the P9, and P6 anchors analogs C84(M→V), C83(RM→KV) and C81(F→V, RM→KV) were synthesized. Peptide C84 induced a significant increase in FL1 that was comparable with D119 (FIG. 5C), suggesting that the presence of a strong anchor at P9 in this peptide is important for induction of a MA2.1 conformational epitope on T2. C83 did not increase further the FL1, suggesting that the substitution R→K may not be critical for reactivity of MA2.1 with HLA-A2. Of note, C81 significantly increased the FL1, suggesting that the presence of V at P6 is important for induction of MA2.1 conformational epitopes. Since the previous data suggest that C85 may interact with HLA-A2, the reactivity of BB7.2 mAb with T2 cells preincubated with the same peptides was examined. The results show that C85 induces an increase in FL1 of cells stained with BB.7.2 (FIG. 5D). The analogs C84 and C81 induced an even higher increase in FL1 of cells reacted with BB.7.2.

To clarify whether (L/I (P2) and V/L (P9) as critical elements for induction of MA2.1 conformational epitopes is restricted to HER-2, a control study analyzed the effect on FL1 of T2 cells stained with MA2.1 of five nonapeptide analogs from the sequence of folate binding protein (FBP) which is also overexpressed in ovarian cancer. The results are presented in FIG. 6. Of five peptides, one (E37) failed to affect MA2.1 epitope expression, three showed a moderate increase similar with C84 regardless that either Leu or Val were present P9, and only one showed a very high increase in FL1. This peptide (E38) has a different P2 (L vs I) from E39 which showed only a moderate increase in FL1 and included I(P6). Two other peptides (E40-E41) containing the groups ALM and MLL at P5–P7 failed to induce an increase in FL1. These results indicate that in addition to the presence of predicted dominant P2 and P9 anchors, induction of conformational MA2.1 epitopes on HLA-A2 also depends on the peptide sequence at P3–P8. It is likely that the presence of certain residues affects the reactivity of MA2.1 mAb with HLA-A2. Therefore MA2.1 epitope expression alone does not necessarily reflect the affinity of peptide binding to MA2.1.

4. Stimulation of Peptide Reactive CTL In Vitro

HER-2 peptides (Table 6) were tested for their ability to stimulate HLA-A2$^+$ PBMC to proliferate in vitro. PBMC from healthy donors were incubated with HER-2 peptides from the groups:41–56, 392–410 and 968–984 for 5 days. With few exceptions, significant cell proliferation was not observed in all 4 PBMC samples from individual donors of different HLA-types including HLA-A2. (S.I. ranged between 0.8–1.5) suggesting that these short peptides were not mitogenic. The exception to these observations was Donor 20.S.I. for D95 was 6.4, for D121 was 4.3, but for the nonamer D119 was only 1.1. Similarly, the S.I. for the longer peptide D96 (41–54) was 2.8 but for the shorter peptide D97 was only 1.5. These differences were statistically significant. Proliferation of PBMC stimulated with peptides in the presence of IL-2 failed to clearly distinguish between peptides that induced lymphocyte proliferation and those that did not, because of the overall increase in the levels of proliferation of both control and peptide stimulated samples.

Figures 7A, 7B, 7C:
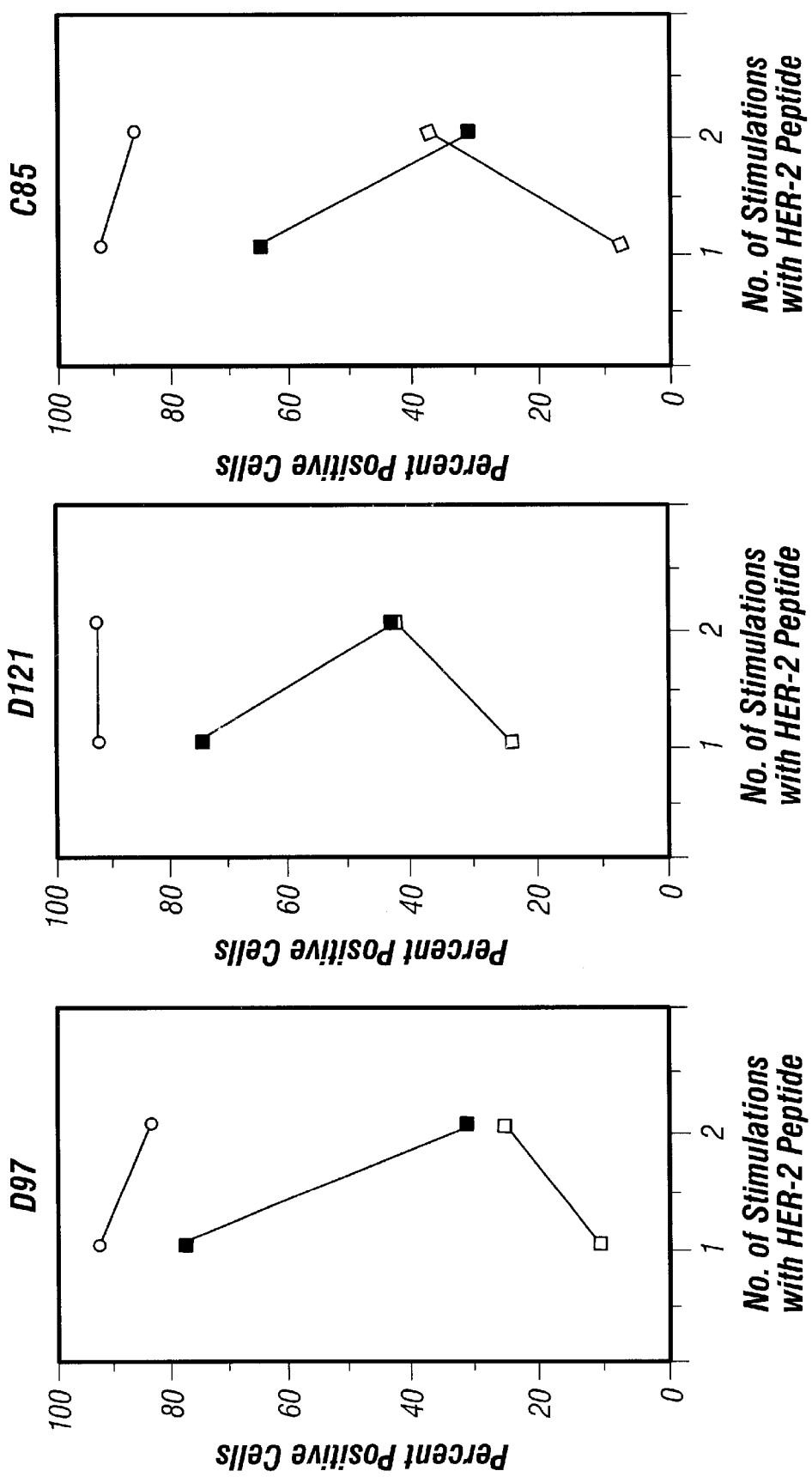
FIG. 7A. Surface phenotype of T-cells from PBMC cultures stimulated with HER-2 peptide D97. Fresh isolated PBMC from healthy volunteers were induced in vitro with HER-2 peptides. T-cell surface phenotypes were determined after one (1) and two (2) stimulations with the same peptide. Immunofluorescence analysis was performed as described in the Materials and methods. Symbols indicate (o—o) CD3+ cells, (■—■) CD8+ cells, and (□—□) CD4+ cells.
FIG. 7B. Surface phenotype of T-cells from PBMC cultures stimulated with HER-2 peptide D121. Studies were performed as described in the legend to FIG. 7A.
FIG. 7C. Surface phenotype of T-cells from PBMC cultures stimulated with HER-2 peptide C85. Studies were performed as described in the legend to FIG. 7A.

To address the question of whether in vitro stimulation of PBMC with HER-2 peptides followed by culture in the presence of IL-2 leads to T-cell phenotype change, the % CD3, CD4, and CD8 expression on the surface of HER-2 peptide-stimulated PBMC were determined. The results of a typical study are shown in FIG. 7A, FIG. 7B and FIG. 7C. Nine days after the first stimulation with either peptide D97 (a decamer containing a nested octapeptide), D121 (a 20-mer containing nested an octapeptide and a nonapeptide) and C85 (nonapeptide) and expansion in IL-2, all cultures showed a significant increase in CD8$^+$ cells and a decrease in CD4$^+$ cells was observed associated with overall cell expansion and growth. This trend continued in all cultures and 10–15 days after a third stimulation, with the same peptide in all cultures, CD4$^+$ cells constituted the dominant (>80%) cell population.

5. Lytic Activity and Specificity of HER-2 Peptide-Stimulated PBMC

To elucidate the ability of HER-2 peptides to induce CTLs in vitro, the ability of HLA-A2$^+$ PBMC cultured in the presence of HER-2 peptides and IL-2 to recognize peptides used as stimulators was determined. HER-2 peptides with different sequences were used as specificity controls. C1R:A2 cells were used as targets because they express only HLA-A2. A first group of peptides selected as stimulators were from the area HER-2:41–56 as follows: D96 and D97 containing the octapeptide:42–49, and D113 and D114 corresponding to the overlapping peptides 48–56 and 47–56. Stimulation and restimulation with irradiated autologous PBMC pulsed with peptide showed mixed results. In certain cases, higher peptide recognition was determined, in others lack of peptide specificity was observed. In most cultures, after the second stimulation with HER-2 peptides, CD4$^+$ cells became the dominant population, and they expressed either LAK type lytic activity or failed to recognize the Ag used for stimulation.

Figures 9A, 9B, 9C:
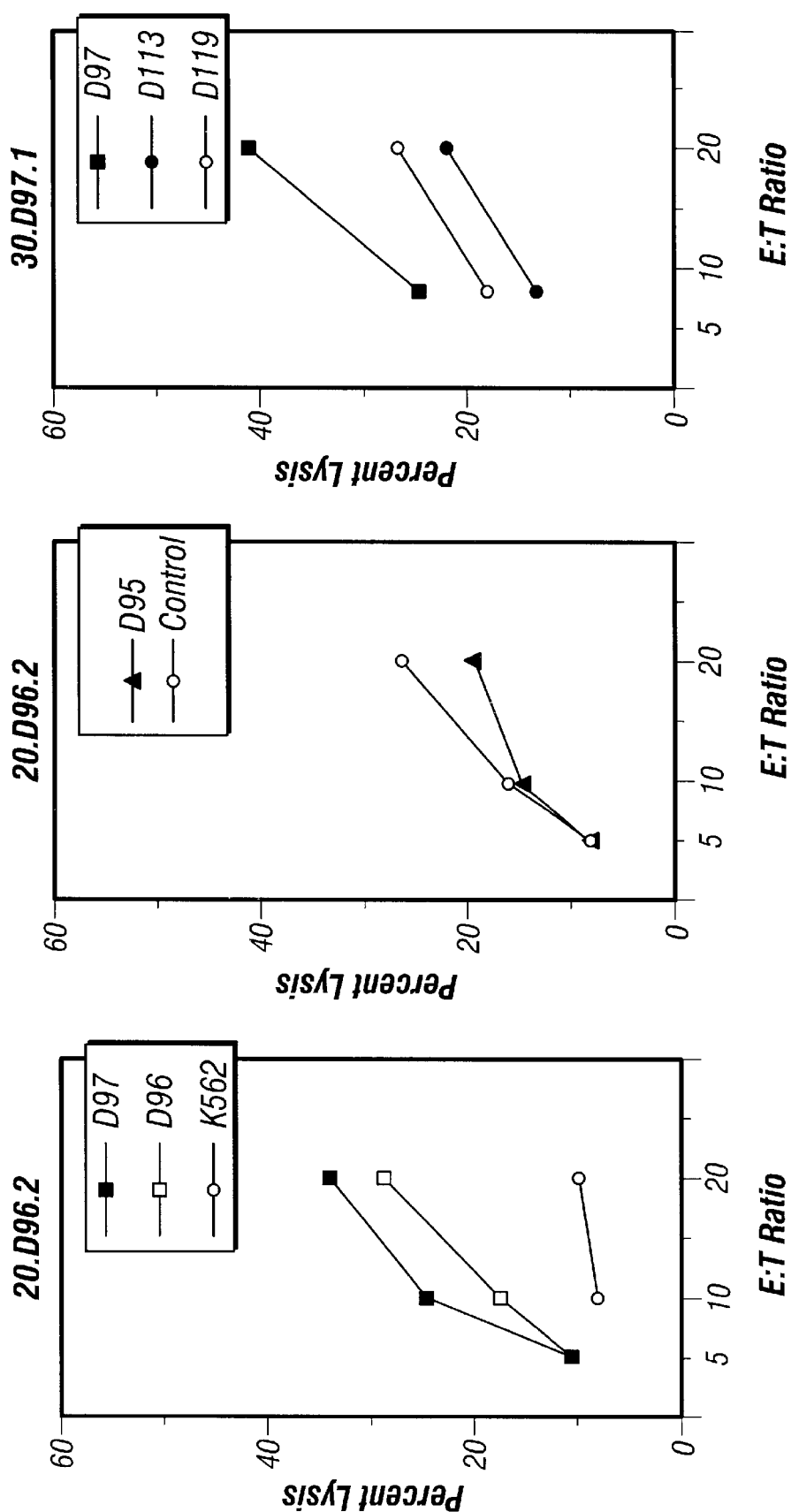
FIG. 9A. CTL induction by HER-2 peptides D96 and D97. PBMC from donor 20 were stimulated two times with D96 (20.D96.2). CTL activity was determined in a 4 h $^{51}$Cr release assay using as targets C1R:A2 cells without addition of exogenous peptide (control) or pulse-labelled with D96 (□), D97 (■), or NK sensitive targets K562 cells were used as an additional control.
FIG. 9B. CTL induction by HER-2 control peptide D95 (▼) peptides. NK sensitive targets K562 cells were used as an additional control.
FIG. 9C. CTL induction by HER-2 peptides. PBMC from donor 30 were induced with D97 peptide (30.D97.1). Seven days later CTL activity of these cells was determined using as targets the peptide used for stimulation (D97) or two HLA-A2 binding peptides with unrelated sequence D113 and D119, as specificity controls.

The results of a typical study that used as targets three HER-2 peptides and as effectors PBMC from donor 20 stimulated either once with D97 or cultured in the same conditions in the absence of HER-2 peptide (as control) are shown in FIG. 8A, FIG. 8B, and FIG. 8C. Control cultures showed low levels of similar lysis of all targets. In contrast, cultures stimulated with D97 showed at 6:1 E/T ratio somewhat higher lysis of targets pulsed with the peptides used for stimulation, than of control peptides D98 (no HLA-A2 anchors) and D99 but the background lysis was relatively high. Similarly when PBMC from the same donor were stimulated with D96 which includes the area HER-2:42–51, higher lysis of targets pulsed with D97 than D96 was observed (FIG. 9A, FIG. 9B, and FIG. 9C). The same cultures showed lower lysis of targets pulsed either with control D95 peptide (not used for stimulation), or control C1R:A2 cells, or the NK sensitive targets K562 cells. D97 stimulated PBMC from the donor 30 showed higher lysis of targets pulsed with D97 than with the overlapping 48–56 and control D119 nonapeptides. The results are shown in FIG. 9A, FIG. 9B, and FIG. 9C. In 2/3, donors peptides D96/D97 induced in vitro CTLs can preferentially recognize the peptide used as stimulator. This suggests that a potential epitope capable of stimulating T-cells in vitro is nested in the area 42–51.

Figure 10A:
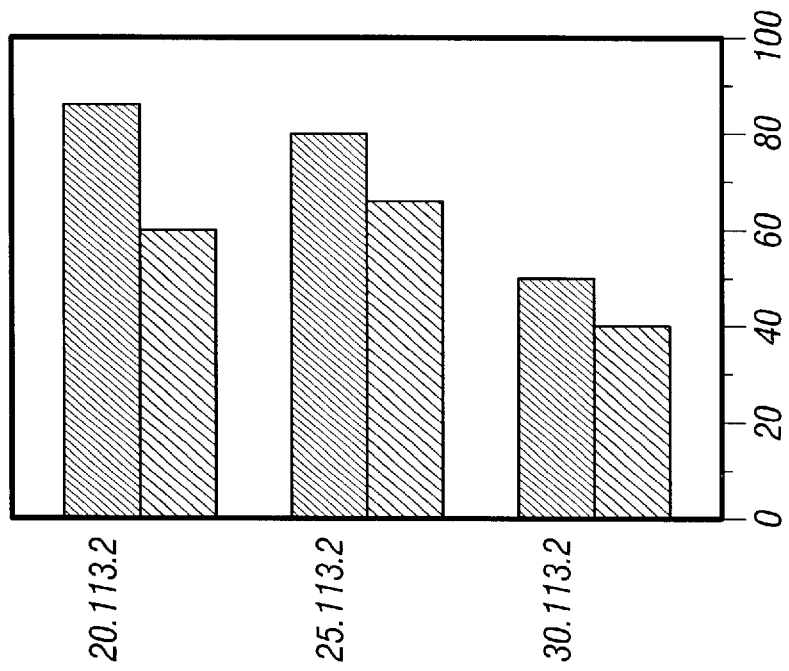
FIG. 10A. CTL induction by HER-2 peptide D113. PBMC from three healthy donors (20, 25 and 30) were induced with D113 peptide. Each culture was restimulated with D113 once. One week later CTL activity was determined using as targets C1R:A2 cells pulsed with D113. The effectors are designated as 20.113.2, 25.113.2 and 30.113.2 to indicate the donor number, the peptide symbol and the number of stimulations with peptide. Experimental conditions were as described in Example 2 and the legends to FIG. 8A and FIG. 9A. E:T ratios were 20:1 (heavy stripes) and 10:1 (medium stripes).
Figure 10B:
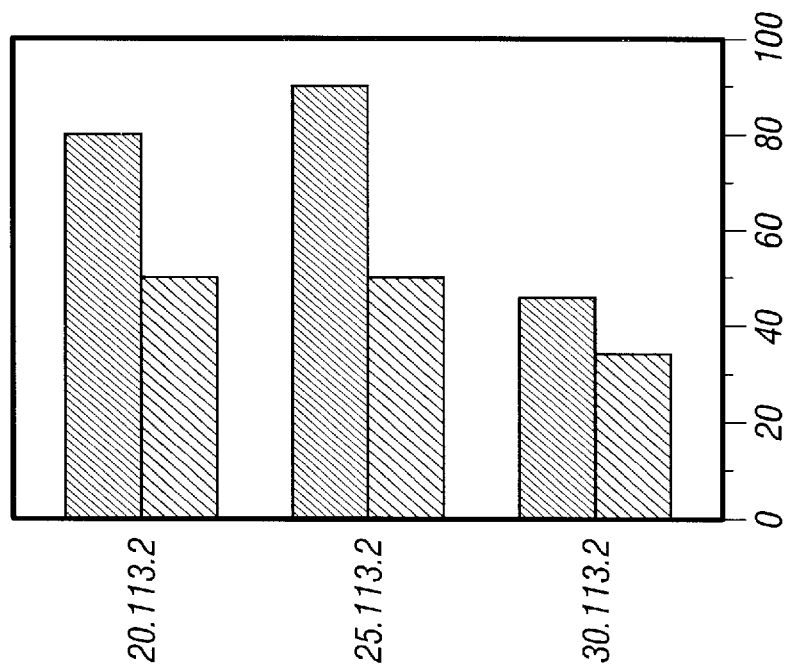
FIG. 10B. CTL induction by HER-2 peptide D113. PBMC from three healthy donors (20, 25 and 30) were induced with D113 peptide. Each culture was restimulated with D113 once. One week later CTL activity was determined using as targets C1R:A2 cells pulsed with control D119 peptide. The effectors are designated as 20.113.2, 25.113.2 and 30.113.2 to indicate the donor number, the peptide symbol and the number of stimulations with peptide. Experimental conditions were as described in Example 2 and the legends to FIG. 8A and FIG. 9A. E:T ratios were 20:1 (heavy stripes) and 10:1 (medium stripes).

Peptide D113 and its mutated analog D114 induced a CTL response which apparently lacked Ag specificity (FIG. 10A and FIG. 10B). Although in 2/3 HLA-A2$^+$ donors, at certain E:T ratios peptide induced CTL showed higher recognition of targets pulsed with D113 than of control D119 peptide, the differences were minimal. These peptide-induced CTL were designated as non-specific. D113, D114 and D115 showed higher increase in reactivity of MA2.1 mAb with HLA-A2 than D96/D97. However they induced less specific CTL than D96/D97. The reasons for these differences are unknown, however the results should be interpreted with caution because of the difficulties in solubilizing D113 and its analogs.

Figure 11C:
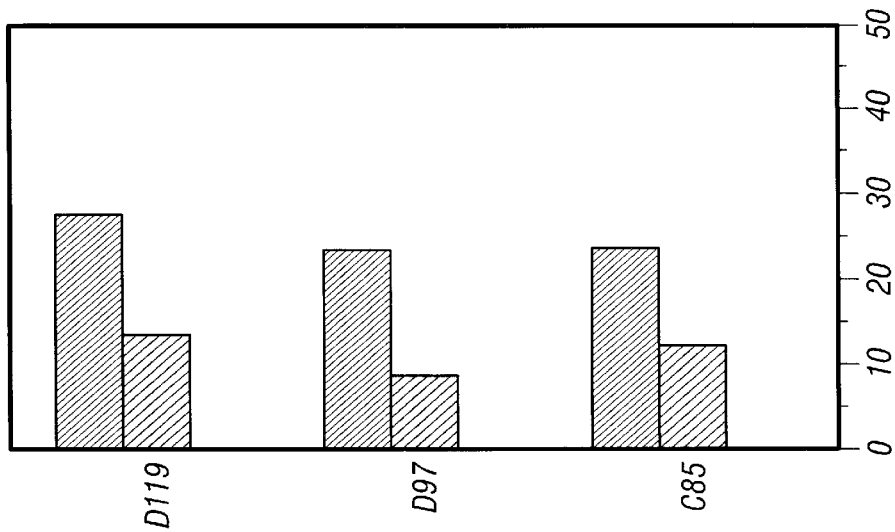
FIG. 11C. CTL induction by HER-2 peptides D121 and D119. PBMC from a healthy donor (25) were induced with D121:HER-2:392–410 or D119:HER-2:402–410 by stimulating with the peptides once (25.119.1). CTL activity was determined using C1R:A2 targets pulsed either with the Ag of interest (D119) or control peptides D95, D99, D97, C85 (Table 5). E:T ratios were 20:1 (heavy stripes), 10:1 (medium stripes) and 3:1 (light stripes).
Figure 11B:
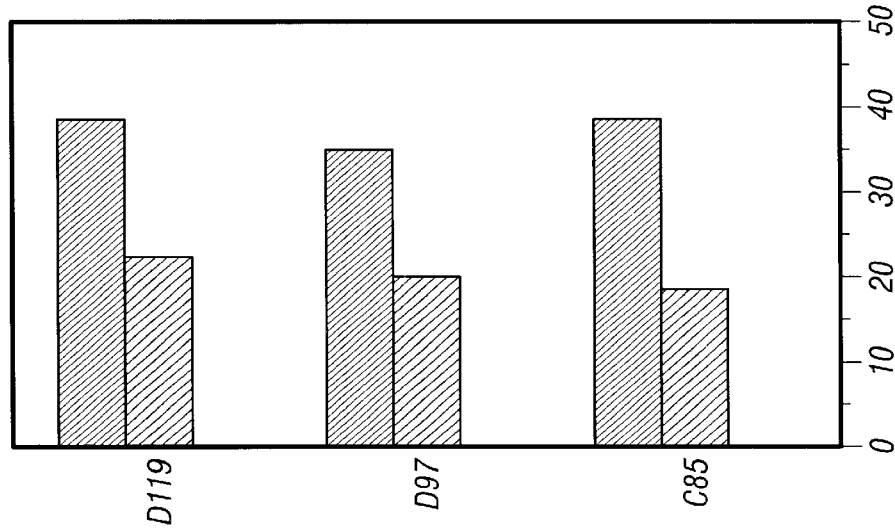
FIG. 11B. CTL induction by HER-2 peptides D121 and D119. PBMC from a healthy donor (25) were induced with D121:HER-2:392–410 or D119:HER-2:402–410 by stimulating with the peptides once (25.121.1). CTL activity was determined using C1R:A2 targets pulsed either with the Ag of interest (D119) or control peptides D95, D99, D97, C85 (Table 5). E:T ratios were 20:1 (heavy stripes), 10:1 (medium stripes) and 3:1 (light stripes).
Figure 11A:
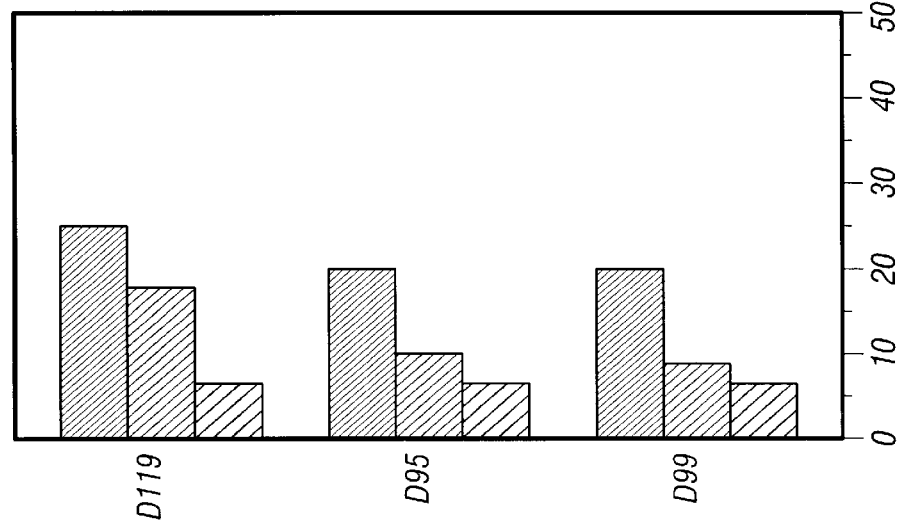
FIG. 11A. CTL induction by HER-2 peptides D121 and D119. PBMC from a healthy donor (20) were induced with D121:HER-2:392–410 or D119:HER-2:402–410 by stimulating with the peptides twice (20.121.2) or once (25.121.1 and 25.119.1 respectively). CTL activity was determined using C1R:A2 targets pulsed either with the Ag of interest (D119) or control peptides D95, D99, D97, C85 (Table 5). E:T ratios were 20:1 (heavy stripes), 10:1 (medium stripes) and 3:1 (light stripes).

The peptide D121 (HER-22:392–411) induced a CTL response that lacked Ag specificity (FIG. 11A). However, D121 stimulated PBMC from donor 20 showed somewhat higher lysis of targets pulsed with the nonapeptide D119 than D121, but this response was short-lived. PBMC from two other donors (25 and 30) stimulated with D121 and D119, were used as effectors to determine the specificity of D119 recognition of every peptide. Similar results were obtained with peptide stimulated PBMC from donor 30. Peptide recognition was also determined in 20 h cytotoxicity assays. No major differences in recognition of targets pulsed with peptides used as stimulator versus control peptides were observed. Similarly D119 was found to increase the reactivity of MA2.1 mAb with HLA-A2 on T2 cells but failed to induce peptide specific CTLs (FIG. 11B and FIG. 11C).

EXAMPLE 3

Synthesis of Novel Universal Immunodominant Peptide Epitopes

A large number of nonapeptides (synthetic analogs) have been constructed, and it has been determined which ones are recognized by CTLs associated with and lysing ovarian tumors. Of more than 15 peptides tested for recognition by three HLA-A2+ CTL lines, the following peptides have been recognized more often. Based on the levels of lysis induced they were designated as high: C85 (2/3); E90 (2/3), E75 (2/3) E71 (2/3), E89 (2/3); and moderate E77 (2/3).

The sequences of these peptides are as follows:

```
C85 = HER-2:971-979 - E L V S E F S R M    (SEQ ID NO:7)
E89 = HER-2:851-859 - V L V K S P N H V    (SEQ ID NO:8)
E71 = HER-2:798-806 - Q L M P Y G C L L    (SEQ ID NO:9)
E90 = HER-2:788-796 - C L T S T V Q L V    (SEQ ID NO:10)
E75 = HER-2:370-378 - K I F G S L A F L    (SEQ ID NO:11)
E77 = HER-2:391-399 - P L Q P E Q L Q V    (SEQ ID NO:12)
```

The ability of these peptides to sensitize targets for lysis by tumor associated CTLs (relative to positive control C85) is shown in Table 7.

These sequences, being immunodominant, can provide universal HER-2 targets and antigens for CTLs in the HLA-A2 system expressed by over 45% of North American population.

Since HER-2 is a self-antigen, during thymic selection, a number of T-cells carrying receptors with high affinity for the HLA-peptide complex are silenced either by elimination ro tolerization. A pre-condition for induction of a high affinity TCR-(MHC+peptide) interactions, is a stable (MHC+peptide) complex. Therefore T-cells reacting with peptides that bind HLA with low affinity and have weak stabilizing effect, are not likely to be eliminated in vivo but they can become CTL targets. However, stabilization of HLA-Class I binding by exogenously added peptide is dependent on introduction of dominant anchors in positions P2 and P9 which are not recognized by TCR. In addition to patenting this concept we found that replacement of Met (P9) stabilize HLA-A2 expression on an indicator line T2 used for these types of studies.

TABLE 7

RECOGNITION OF HER-2 PEPTIDES BY OVARIAN TUMOR ASSOCIATED CYTOTOXIC T LYMPHOCYTES

| CTL-24 | % of C85[a] |
|---|---|
| High | |
| C85[b] | 1.000 |
| E90 | 0.885 |
| E75 | 0.850 |
| Moderate | |
| E77 | 0.759 |
| E89 | 0.734 |
| E71 | 0.625 |
| Negative | |
| D113 | 0.095 |
| D99 | 0.050 |
| D97 | −0.025 |
| CTL-34 | % of C85 |
| High | |
| C85 | 1.000 |
| E90 | 1.149 |
| E89 | 1.149 |
| Moderate | |
| E71 | 0.600 |
| E77 | 0.300 |
| CTL-16 | |
| High | |
| E75 | >10.00[c] |

[a]The levels of targets lysis by CTL in the presence of each HER-2 peptide are shown as % of positive control (C85 peptide) recognition by CTL.
[b]E75 was the only peptide significantly recognized by this CTL line.

C85=ELVSEFSRM (SEQ ID NO:7) is the natural nonapeptide recognized by CTL. Peptides C84=ELVSEFSR$\underline{V}$, (SEQ ID NO:6) and C83=ELVSEFS$\underline{K}$V (SEQ ID NO:5) are analogs with strengthened P9 and P8. C84 also can specifically inhibit tumor lysis by peptide induced CTL. Furthermore, Leu (P2) is a dominant anchor, but E (P1) may be electrostatically rejected by residues that form the MHC class I binding pocket. Thus replacement of E→G (P1) (neutral) or E→K (P1, positive charge) are also expected to stabilize the interaction, while the residues being buried in the pocket, are expected not to affect CTL recognition.

The analogs with sequences C91=GLVSEFSRV, (SEQ ID NO:4) and C92=KLVSEFSRV (SEQ ID NO:3) are also compositions of the present invention. In addition, substitutions at P4 (S→K) and P6 (F→V) affect residues that are expected to interact with TCR. The analog C81=ELVSE$\underline{V}$ $\underline{K}$V (SEQ ID NO:2) stabilized HLA-A2 more than C84, while C82: ELV$\underline{K}$E$\underline{V}$S$\underline{K}$V (SEQ ID NO:1) although binds HLA-A2 is no longer recognized by C84 reactive CTL. Both C81 and C82 can form the core for antagonists of HER-2 reactive CTLs (to control and stop CTL reactions), and as such represent the first "universal" antagonists reported for stimulating CTLs.

Peptide D113, HLYQGCQVV (SEQ ID NO:17), is the natural nonapeptide HER-2:42–51. D113 stabilizes HLA-A2 on indicator T2 cells. The novel synthetic peptide analog, D114, R$\underline{L}$LYQGCQVV (SEQ ID NO:18), shows little improvement on stabilization of HLA-A2, but the novel peptide, D115, $\underline{G}$LYQGCQVV (SEQ ID NO:19), shows significantly higher improvement which confirmed the predictions above.

EXAMPLE 4

Peptide Formulations

Peptides containing the epitope motifs described herein are contemplated for use in therapeutics to provide universal HER-2 targets and antigens for CTLs in the HLA-A2 system expressed by over 45% of the North American population. The development of therapeutics based on these novel sequences provides induction of tumor reactive immune cells in vivo through the formulation of synthetic cancer vaccines, as well as induction of tumor-reactive T-cells in vitro through either peptide-mediated (e.g., lipopeptide) or cell-mediated (e.g., EBV-B lines using either autologous or HLA-A2 transfectants where the gene for the peptide of interest is introduced, and the peptide is expressed associated with HLA-A2 on the surface). The use of these novel peptides as components of vaccines to prevent, or lessen the chance of cancer progression is also contemplated.

The peptides contemplated for use, being smaller than other compositions, such as envelope proteins, will have improved bioavailability and half lives. If desired, stability examinations may be performed on the peptides, including, e.g., pre-incubation in human serum and plasma; treatment with various proteases; and also temperature- and pH-stability analyses. If found to be necessary, the stability of the synthetic peptides may be enhanced by any one of a variety of methods such as, for example, employing D-amino acids in place of L-amino acids for peptide synthesis; using blocking groups like t-boc and the like; or encapsulating the peptides within liposomes. The bioavailability of select mixtures of peptides may also be determined by injecting radio-labeled peptides into experimental animals, such as mice and/or Rhesus monkeys, and subsequently analyzing their tissue distribution.

If stability enhancement was desired, it is contemplated that the use of dextrorotary amino acids (D-amino acids) would be advantageous as this would result in even longer bioavailability due to the inability of proteases to attack these types of structures. The peptides of the present invention may also be further stabilized, for example, by the addition of groups to the N- or C-termini, such as by acylation or amination. If desired, the peptides could even be in the form of lipid-tailed peptides, formulated into surfactant-like micelles, or other peptide multimers. The preparation of peptide multimers and surfactant-like micelles is described in detail in U.S. Ser. No. 07/945,865, incorporated herein by reference. The compositions of the present invention are contemplated to be particularly advantageous for use in economical and safe anti-tumor/anti-cancer therapeutics, and specific therapeutic formulations may be tested in experimental animal models, such as mice, rats, rabbits, guinea pigs, cats, goats, Rhesus monkeys, chimpanzees, and the like, in order to determine more precisely the dosage forms required.

In addition to the peptidyl compounds described herein, the inventors also contemplate that other sterically similar compounds may be formulated to mimic the key portions of the peptide structure and that such compounds may also be used in the same manner as the peptides of the invention. This may be achieved by the techniques of modelling and chemical design known to those of skill in the art. For example, esterification and other alkylations may be employed to modify the terminus of a peptide to mimic a particular terminal motif structure. It will be understood that all such sterically similar constructs fall within the scope of the present invention.

Therapeutic or pharmacological compositions of the present invention will generally comprise an effective amount of a CTL-stimulating peptide or peptides, dissolved or dispersed in a pharmaceutically acceptable medium. The phrase "pharmaceutically acceptable" refers to molecular entities and compositions that do not produce an allergic, toxic, or otherwise adverse reaction when administered to a human. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated.

Supplementary active ingredients can also be incorporated into the therapeutic compositions of the present invention. For example, the stimulatory peptides may also be combined with peptides including cytotoxic T-cell- or T-helper-cell-inducing epitopes (as disclosed in U.S. Ser. No. 07/945,865; incorporated herein by reference) to create peptide cocktails for immunization and treatment.

The preparation of pharmaceutical or pharmacological compositions containing a CTL-stimulating peptide or peptides, including dextrorotatory peptides, as active ingredients will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalents and the like.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile solutions suitable for intravenous administration are preferred in certain embodiments and are contemplated to be particularly effective in stimulating CTLs and/or producing an immune response in an animal. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

A peptide or peptides can be formulated into a composition in a neutral or salt form. Pharmaceutically acceptable salts, include the acid addition salts (formed with the free amino groups of the peptide) and which are formed with inorganic acids such as, e.g., hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

The carrier can also be a solvent or dispersion medium containing, e.g., water, ethanol, polyol (for example, glycerol, propylene glycol, and liquid polyethylene glycol, and the like), suitable mixtures thereof, and vegetable oils. The proper fluidity can be maintained by inter alia the use of a coating, such as lecithin, by the maintenance of the required particle size in the case of dispersion and by the use of surfactants. The prevention of the action of microorganisms can be brought inter alia by various antibacterial ad antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more- or highly-concentrated solutions for intramuscular injection is also contemplated. This is envisioned to have particular utility in facilitating the treatment of needle stick injuries to animals or even humans. In this regard, the use of DMSO as solvent is preferred as this will result in extremely rapid penetration, delivering high concentrations of the active peptide, peptides or agents to a small area.

The use of sterile formulations, such as saline-based washes, by veterinarians, technicians, surgeons, physicians or health care workers to cleanse a particular area in the operating field may also be particularly useful. Therapeutic formulations in accordance with the present invention may also be reconstituted in the form of mouthwashes, including the peptides alone, or in conjunction with antifungal reagents. Inhalant forms are also envisioned, which again, may contain active peptides or agents alone, or in conjunction with other agents, such as, e.g., pentamidine. The therapeutic formulations of the invention may also be prepared in forms suitable for topical administration, such as in cremes and lotions.

Buffered ophthalmic solutions also fall within the scope of the invention, and may be created in accordance with conventional pharmaceutical practice, see for example "Remington's Pharmaceutical Sciences" 15th Edition, pages 1488 to 1501 (Mack Publishing Co., Easton, Pa.). Suitable ophthalmic preparations will generally contain a novel dipeptide, peptide or agent as disclosed herein in a concentration from about 0.01 to about 1% by weight, and preferably from about 0.05 to about 0.5%, in a pharmaceutically acceptable solution, suspension or ointment. The ophthalmic preparation will preferably be in the form of a sterile buffered solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9±0.2%. Suitable antioxidants and stabilizers include sodium bisulfite, sodium metabisulfite, sodium thiosulfate, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed. As used herein, "pharmacologically effective amount" means an amount of composition is used that contains an amount of a peptide or peptides sufficient to significantly stimulate a CTL or generate an immune response in an animal.

In this context, the quantity of peptide(s) and volume of composition to be administered depends on the host animal to be treated, such as, the capacity of the host animal's immune system to produce an immune response. Precise amounts of active peptide required to be administered depend on the judgment of the practitioner and are peculiar to each individual.

A minimal volume of a composition required to disperse the peptide is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580).

In certain embodiments, active compounds may be administered orally. This is contemplated for agents that are generally resistant, or have been rendered resistant, to proteolysis by digestive enzymes. Such compounds are contemplated to include chemically designed or modified agents; dextrorotatory peptides; and peptide and liposomal formulations in timed-release capsules to avoid peptidase, protease and/or lipase degradation.

Oral formulations may include compounds in combination with an inert diluent or an edible carrier which may be assimilated; those enclosed in hard- or soft-shell gelatin capsules; those compressed into tablets; or those incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should generally contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

Tablets, troches, pills, capsules and the like may also contain the following: a binder, as gum tragacanth, acacia, corn starch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparaben as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The peptides may be used in their immunizing capacity by administering an amount effective to generate an immune response in an animal. In this sense, such an "amount effective to generate an immune response" means an amount of composition that contains a peptide or peptide mixture sufficient to significantly produce an antigenic response in said animal.

EXAMPLE 5

Methods for Protein Size Determination and Gel Chromatography

The amino acid sequences disclosed herein, and particularly the tripeptide motifs and multimers thereof, find particular use in the determination of molecular weights of small polypeptides. These peptides represent a significant improvement over commercially-available protein standards in this area owing to their small size and, since their amino acid sequence is known, their precise molecular weight is readily determined.

1. SDS-PAGE Analysis of Proteins

Commercially-available protein standards for SDS-PAGE or gel filtration chromatography typically have a range of 3,000 to 200,000 Da (Gibco BRL, Bethesda, Md.), and as such, are not useful in the characterization of proteins having molecular weights of about 300 to about 3,000 Da. By employing peptides of the present invention (e.g., SEQ ID NOS:1–15) and multimers thereof, a range of suitable low-molecular weight standards may be readily prepared. Such a molecular weight ladder mixture may be employed either in SDS-PAGE or gel filtration protocols which are well-known to those of skill in the art (see e.g., Wood, 1981).

2. Paper and Thin-layer Chromatography

In a similar fashion, the polypeptides, and more particularly the tripeptide motifs, of the present invention are readily employed as standards in the identification of small molecular-weight polypeptides using chromatographic separation. In preferred embodiments, paper chromatography is utilized and proteins are subsequently visualized after reaction with ninhydrin. More preferred is the use of thin-layer chromatography in either one or two dimensions.

3. Gel Filtration Chromatography

The polypeptides of the present invention provide excellent standards for the calibration of chromatographic columns used in the separation of low molecular-weight polypeptides. In particular, the tripeptide motifs, and multimers thereof, find important use in the standardization of low-molecular weight-range columns (Rawn, 1983). These chromatography columns may include a filtration medium having the capacity to fractionate any protein of interest and the polypeptides of the present invention. Chromatographic media such as G-50 or G-25 Sephadex® resins (approximate fractionation range of 1,500–30,000 and 100–5,000 Da, respectively) may be used for generalized separation, or in cases where the approximate molecular weight of the protein of interest is known, a medium having a narrower fractionation range (e.g., G-10 Sephadex® [0–700 Da separation range] or G-15 Sephadex® [0–1,500 Da separation range]) may be employed. A regression line of the elution position versus the log of the molecular weight is established using the peptides of the present invention, and the molecular weight of the protein of interest is then determined from this graph. Detailed protocols for preparation, calibration, and execution of these columns is well-known to those of skill in the art (see e.g., Wood, 1981).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text.

Aebersold et al., "Lysis of autologous melanoma cells by tumor-infiltrating lymphocytes: association with clinical response," *J. Natl. Cancer Inst.*, 83:932–937, 1991.

Alexander et al., "Correlation between CD8 dependency and determinant density using peptide-induced, Ld-restricted cytotoxic T lymphocytes," *J. Exp. Med.*, 173:849–858, 1991.

Anderson et al., "Intracellular transport of Class I MHC molecules in antigen processing mutant cell lines," *J. Immunol.*, 151:3407–3419, 1993.

Anderson et al., *Mol. Immunol.*, 29:1089, 1992.

Ausubel, F. M. et al., "Current Protocols in Molecular Biology," John Wiley & Sons, New York, 1989.

Bednarek et al., "The minimum peptide epitope from the influenza virus matrix protein: extra and intracellular loading of HLA-A2," *J. Immunol.*, 147:4047–4053, 1991.

Bednarek al., "Soluble HLA-A2.1 restricted peptides that are recognized by influenza virus specific cytotoxic T lymphocytes," *J. Immunol. Meth.*, 139:41–47, 1991.

Bowness et al., *Eur. J. Immunol.*, 23:1417, 1993.

Brichard et al., *J. Exp. Med.*, 178:489, 1993.

Brock et al., "Biology of Microorganisms" 7th Edition, Prentice Hall, Inc., Englewood Cliffs, N.J., 1994.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Carbone et al., "Induction of cytotoxic T lymphocytes by primary in vitro stimulation with peptides," *J. Exp. Med.*, 167:1767–1779, 1988.

Coakley and James, "A Simple Linear Transform for the Folin-Lowry Protein Calibration Curve to 1.0 mg/ml," *Anal. Biochem.* 85:90–97, 1978.

DeLisi and Berzofsky, "T-cell antigenic sites tend to be amphipathic structures," *Proc. Natl. Acad. Sci. USA*, 82:7048–7052, 1985.

Dibrino et al., *J. Immunol.*, 152:620, 1994.

Falk et al., "Allele-specific motifs revealed by sequencing of self-peptides eluted from MHC molecules," *Nature*, 351:290–296, 1991.

Fisk et al., "Oligopeptide induction of a cytotoxic T lymphocyte response to HER-2/Neu proto-oncogene in vitro," *Cell. Immunol.* 157:415–427, 1994a.

Fisk et al., "Sequence motifs of human HER-2 proto-oncogene important for peptide binding to HLA-A2," *Int. J. Oncol.* 5:51–63, 1994b.

Fisk et al., "Oligopeptide induction of a cytotoxic T lymphocyte response to HER-2/neu proto-oncogene product in vitro," *Proc. AACR*, 35:498, 1994c.

Gammon et al., "Endogenous loading of HLA-A2 molecules with an analog of the influenza virus matrix protein-derived peptide and its inhibition by an exogenous peptide antagonist," *J. Immunol.*, 148:7–12, 1992.

Gefter et al., *Somatic Cell Genet.* 3:231–236, 1977.

Gendler et al., *J. Biol. Chem.*, 263:12820, 1988.

Goding, "Monoclonal Antibodies: Principles and Practice," pp. 60–74. 2nd Edition, Academic Press, Orlando, Fla., 1986.

Grimm et al., *J. Exp. Med.*, 155:1823, 1982.

Harlow, E. and Lane, D. "Antibodies: A Laboratory Manual," Cold Spring Harbor Laboratory, Cold Spring Harbor, N.Y., 1988.

Hill et al., *Nature*, 360:434, 1992.

Hogquist et al., "Peptide variants reveal how antibodies recognize major histocompatibility complex class I," *Eur. J. Immunol.*, 23:3028–3036, 1993.

Houbiers et al., "In vitro induction of human cytotoxic T lymphocyte responses against peptides of mutant and wild-type p53," *Eur. J. Immunol.*, 23:2072–2077, 1993.

Hu et al., *J. Exp. Med.*, 177:1681, 1993.

Ioannides et al., "Cytotoxic T-cell clones isolated from ovarian tumor-infiltrating lymphocytes recognize multiple antigenic epitopes on autologous tumor cells," *J. Immunol.*, 146:1700–1707, 1991.

Ioannides et al., "Cytotoxic T-cells isolated from ovarian malignant ascites recognize a peptide derived from the HER-2/neu proto onco gene," *Cell Immunol.*, 136:225–234, 1993.

Ioannides et al., "T-cell recognition of oncogene products," *Mol. Carcinogen*, 6:77–81, 1992.

Ioannides et al., "Tumor cytolysis by lymphocytes infiltrating ovarian malignant ascites," *Cancer Res.*, 51:4257–4264, 1991.

Ioannides et al., *Scand. J. Immunol.*, 37:413, 1993.

Jacobson et al., *J. Virol.*, 63:1756, 1989.

Jameson & Wolf, *Compu. Appl. Biosci.*, 4(1):181–6, 1988.

Jerome et al., *Cancer Res.*, 51:2908, 1991.

Jerome et al., *J. Immunol.*, 151:1654, 1993.

Kaiser and Kezdy, "Amphiphilic secondary structure: Design of peptide hormones," *Science*, 223:249–255, 1984.

Kohler and Milstein, *Eur. J. Immunol.* 6:511–519, 1976.

Kohler and Milstein, Nature 256:495–497, 1975.

Kos and Müllbacher, *Eur. J. Immunol.*, 22:3183, 1992.

Kyte and Doolittle, 1982

Letessier et al., *Cancer Res.*, 51:3891, 1991.

Lowry et al., "Protein Measurement with the Folin Phenol Reagent," *J. Biol. Chem.* 193:265–275, 1951.

Madden et al., "The antigenic identity of peptide-MHC complexes: a comparison of the conformations of five viral peptides presented by HLA-A2," *Cell*, 75:693–708, 1993.

Maloy, S.R., "Experimental Techniques in Bacterial Genetics" Jones and Bartlett Publishers, Boston, Mass., 1990.

Maloy et al., "Microbial Genetics" 2nd Edition. Jones and Barlett Publishers, Boston, Mass., 1994.

Marincola et al., *Cancer Res.*, 83:932, 1991.

Mullis, K., U.S. Pat. No. 4,683,202, Jul. 28, 1987.

Mullis, K. et al., U.S. Pat. No. 4,683,195, Jul. 28, 1987.

Ohno, Proc. Natl. Acad. Sci. USA, 88:3065, 1991.

Parker et al., "Sequence motifs important for peptide binding to the human MHC class I molecule, HLA-A2," *J. Immunol.*, 149:3580–3587, 1992.

Parmiani, "Tumor immunity as autoimmunity: tumor antigens include normal self proteins which stimulate anergic peripheral T-cells," *Immunol. Today*, 14:536–538, 1993.

Prokop, A., and Bajpai, R. K. "Recombinant DNA Technology I" *Ann. N.Y. Acad. Sci.* vol. 646, 1991.

Ratner and Clark, *J. Immunol.*, 150:4303, 1993.

Rawn, J. D. "Biochemistry" Harper & Row Publishers, New York, 1983.

Rosenberg et al., "Use of tumor-infiltrating lymphocytes and interleukin-2 in the immunotherapy of patients with metastatic melanoma," *N. Engl. J. Med.*, 319:1676–1680, 1988.

Rothbard and Taylor, "A sequence common to T-cell epitopes," *EMBO J.*, 7:93–100, 1988.

Salter and Creswell, "Impaired assembly and transport of HLA-A and -B antigens in a mutant T×B cell hybrid," *EMBO J.*, 5:943–949, 1986.

Salter et al., "In vitro mutagenesis at a single residue introduces B- and T-cell epitopes into a class I HLA molecule," *J. Exp. Med.*, 166:283–288, 1987.

Sambrook, J. et al., "Molecular Cloning: A Laboratory Manual," Cold Spring Harbor Laboratory, Cold Spring Harbor, N.Y., 1989.

Santos-Aguado et al., "Molecular characterization of serologic recognition sites in the human HLA-A2 molecule," *J. Immunol.*, 141:2811–2818, 1988.

Saper et al., "Refined structure of the human histocompatibility antigen HLA-A2 at 2, 6 Å resolution," *J. Mol. Biol.*, 219:277–319, 1991.

Schild et al., "Fine specificity of cytotoxic T lymphocytes primed in vivo either with virus or synthetic lipopeptide vaccine or primed in vitro with peptide," *J. Exp. Med.*, 174:1665–1668, 1991.

Schmidt et al., "Oligopeptide induction of a secondary cytotoxic T-cell response to Epstein-Barr virus in vitro," *Scand. J. Immunol.*, 33:411–420, 1991.

Segal, I. H., "Biochemical Calculations" 2nd Edition. John Wiley & Sons, New York, 1976.

Sherman et al., *J. Exp. Med.*, 175:1221, 1992.

Slamon et al., "Studies of the HER-2/neu proto-oncogene in human breast and ovarian cancer," *Science*, 244:707–712, 1989.

Stauss et al., "Induction of cytotoxic T lymphocytes with peptides in vitro: Identification of candidate T-cell epitopes in human papilloma virus," *Proc. Natl. Acad. Sci. USA*, 89:7871–7875, 1992.

Steinman, *Annu. Rev. Immunol.*, 9:271, 1991.

Suhrbier et al., *J. Immunol.*, 150:2169, 1993.

Walden and Eisen, *Proc. Natl. Acad. Sci. USA*, 87:9015, 1990.

Winter et al., *J. Immunol.*, 146:3508, 1991.

Wolf et al., *Compu. Appl. Biosci.*, 4(1):187–91 1988.

Wolfel et al., *Int. J. Cancer*, 54:636, 1993.

Wood, R. A., "Metabolism," In Manual of Methods for General Bacteriology, (Gerhardt, Murray, Costilow, Nester, Wood, Krieg, and Phillips, Eds.) American Society for Microbiology, Washington, D.C., 1981.

Yamamoto et al., "Similarity of protein encoded by the human c-erb-B-2 gene to epidermal growth factor receptor," *Nature*, 319:230–234, 1986.

Young and Davis, "Efficient Isolation of Genes by Using Antibody Probes," *Proc. Natl. Acad. Sci. USA*, 80:1194–1198, 1983.

Zweerink et al., "Presentation of endogenous peptides to MHC class I-restricted cytotoxic T lymphocytes in transport deletion mutant T2 cells," *J. Immunol.*, 150:1763–1771, 1993.

What is claimed is:

1. A purified peptide comprising the amino acid sequence of SEQ ID NO:11, wherein said peptide induces Her-2 peptide reactive cytotoxic T-lymphocytes.

2. The purified peptide of claim 1 consisting of the amino acid sequence of SEQ ID NO:11.

3. A pharmaceutical composition comprising the peptide of SEQ ID NO:11 in a pharmaceutical acceptable excipient, wherein said peptide induces Her-2 peptide reactive cytotoxic T-lymphocytes.

4. The peptide of claim 1, further defined as a peptide of between 9 and 20 amino acid residues in length.

5. The peptide of claim 4, further defined as a peptide of between 9 and 15 amino acid residues in length.

6. The peptide of claim 5, further defined as a peptide of 9 or 10 amino acid residues in length.

7. A composition comprising a peptide including the amino acid sequence of SEQ ID NO:11, wherein said peptide induces Her-2 peptide reactive cytotoxic T-lymphocytes.

8. The composition of claim 7, wherein the peptide is between 9 and 20 amino acid residues in length.

9. The composition of claim 8, wherein the peptide is between 9 and 15 amino acid residues in length.

10. The composition of claim 9, wherein the peptide is 9 or 10 amino acid residues in length.

11. The composition of claim 7, further comprising a peptide including the amino acid sequence of SEQ ID NO:7.

12. The composition of claim 7, further comprising a peptide including the amino acid sequence of SEQ ID NO:8.

13. The composition of claim 7, further comprising a peptide including the amino acid sequence of SEQ ID NO:10.

14. The composition of claim 11, further comprising a peptide including the amino acid sequence of SEQ ID NO:8.

15. The composition of claim 14, further comprising a peptide including the amino acid sequence of SEQ ID NO:10.

16. The composition of claim 11, further comprising a peptide including the amino acid sequence of SEQ ID NO:10.

17. The composition of claim 12, further comprising a peptide including the amino acid sequence of SEQ ID NO:10.

18. The pharmaceutical composition of claim 3, further comprising a peptide including the amino acid sequence of SEQ ID NO:1.

19. The pharmaceutical composition of claim 3, further comprising a peptide including the amino acid sequence of SEQ ID NO:2.

20. The pharmaceutical composition of claim 3, further comprising a peptide including the amino acid sequence of SEQ ID NO:3.

21. The pharmaceutical composition of claim 3, further comprising a peptide including the amino acid sequence of SEQ ID NO:4.

22. The pharmaceutical composition of claim 3, further comprising a peptide including the amino acid sequence of SEQ ID NO:5.

23. The pharmaceutical composition of claim 3, further comprising a peptide including the amino acid sequence of SEQ ID NO:6.

24. The pharmaceutical composition of claim 3, further comprising a peptide including the amino acid sequence of SEQ ID NO:9.

25. The pharmaceutical composition of claim 3, further comprising a peptide including the amino acid sequence of SEQ ID NO:18.

26. The pharmaceutical composition of claim 3, further comprising a peptide including the amino acid sequence of SEQ ID NO:19.

* * * * *